US009617243B2

(12) United States Patent
McMillen et al.

(10) Patent No.: US 9,617,243 B2
(45) Date of Patent: Apr. 11, 2017

(54) AMINOPYRIDYLOXYPYRAZOLE COMPOUNDS

(71) Applicant: ELi Lilly and Company, Indianapolis, IN (US)

(72) Inventors: William T. McMillen, McCordsville, IN (US); Sajan Joseph, Carmel, IN (US); Huaxing Pei, Carmel, IN (US); Jason Scott Sawyer, Indianapolis, IN (US); Gaiying Zhao, Westfield, IN (US); David A. Coates, Indianapolis, IN (US); Craig D. Wolfangel, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/870,033

(22) Filed: Sep. 30, 2015

(65) Prior Publication Data

US 2016/0096823 A1 Apr. 7, 2016

Related U.S. Application Data

(60) Provisional application No. 62/060,724, filed on Oct. 7, 2014.

(51) Int. Cl.
*C07D 405/14* (2006.01)
*C07D 401/12* (2006.01)
*C07D 401/14* (2006.01)

(52) U.S. Cl.
CPC ......... *C07D 401/12* (2013.01); *C07D 401/14* (2013.01); *C07D 405/14* (2013.01)

(58) Field of Classification Search
CPC .................................................... C07D 405/14
USPC ........................................... 546/256; 514/333
See application file for complete search history.

(56) References Cited

FOREIGN PATENT DOCUMENTS

| | | | |
|---|---|---|---|
| WO | 02094833 | A1 | 11/2002 |
| WO | 2004048382 | A1 | 6/2004 |
| WO | 2004/111036 | | 12/2004 |
| WO | 2009022171 | A1 | 2/2009 |
| WO | 2012002680 | A2 | 1/2012 |
| WO | 2013/086397 | | 6/2013 |
| WO | 2015089800 | A1 | 6/2015 |
| WO | 2015094913 | A1 | 6/2015 |

OTHER PUBLICATIONS

Steiner, "Transforming growth, etc.," World J Urol (1995) 13:329-336.*
Wilson et al., "Pulmonary fibrosis, etc.," Mucosallmmunology, 2(2), 2009, 103-121.*
Glick, TGFbetal, etc., Cancer Biology & Therapy, 2004:3(3), 276-283.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Golub et al, Science, vol. 286, Oct. 15, 1999, pp. 531-537.*
Robinson' "Medical Therapy, etc.," Eur. J. Sirg. 1998: Suppl 582:90-98.*
Sawyer. J.S.,et al., Synthesis abd activity of new aryl- and heteroaryl-substituted pyrazole inhibitors of the transforming growth factor-beta type I receptor kinase domain. Journal of Medicinal Chemistry, American Chemical Society, US, V. 46, No. 19, Sep. 11, 2003, pp. 3953-3956.

* cited by examiner

*Primary Examiner* — Patricia L Morris
(74) *Attorney, Agent, or Firm* — Tina M. Tucker

(57) ABSTRACT

The present invention relates to novel aminopyridyloxypyrazole compounds that inhibit the activity of transforming growth factor beta receptor 1 (TGFβR1), pharmaceutical compositions comprising the compounds, and methods of using the compounds to treat cancer, preferably colon cancer, melanoma, hepatocellular carcinoma, renal cancer, glioblastoma, pancreatic cancer, myelodysplastic syndrome, lung cancer, and gastric cancer, and/or fibrosis, preferably liver fibrosis and chronic kidney disease.

12 Claims, No Drawings

AMINOPYRIDYLOXYPYRAZOLE COMPOUNDS

The present invention relates to novel aminopyridyloxypyrazole compounds that inhibit activity of transforming growth factor beta receptor 1 (TGFβR1), pharmaceutical compositions comprising the compounds, and methods of using the compounds to treat cancer, preferably colon cancer, melanoma, hepatocellular carcinoma (HCC), renal cancer, glioblastoma (GBM), pancreatic cancer, myelodysplastic syndrome (MDS), lung cancer, and gastric cancer, and/or fibrosis, preferably liver fibrosis and chronic kidney disease.

Transforming growth factor beta (TGF-beta or TGFβ) is a multi-functional cytokine which binds to the heteromeric complexes of TGF-beta type I and type II serine/threonine kinase receptors and activates the TGF-beta receptor complex, which phosphorylates and activates SMAD2 and SMAD3, which then associate with SMAD4 and migrate into the nucleus and regulate expression of different target genes. Key players of TGF-beta receptor signal transduction pathway include TGFβ1, TGFβ2, TGFβ3, TGFβR1, TGFβR2, SMADs, SnoN, SARA, SKI, DAB, TRAP, TAK1, SMIF, E2F4, E2F5, RBL1, RBL2, RB1, TFDP1, TFDP2, SMURF1, SMURF2, P300, CBP, and JUN. The SMAD mediated TGF-beta receptor pathway regulates various cellular and physiological processes such as proliferation, differentiation, growth, migration, myelination, cell cycle arrest, apoptosis and development.

Small molecule inhibitors of TGFβR1 are already known in the art for the treatment of cancer and/or fibrosis. See for example, WO2012/002680, WO2009/022171, WO2004/048382, and WO2002/094833. Unfortunately, there is no known curative treatments for many types of cancers or fibrosis. It would be desirable to have additional small molecule inhibitors of TGFβR1 for the treatment of cancer, preferably colon cancer, melanoma, hepatocellular carcinoma (HCC), renal cancer, glioblastoma (GBM), pancreatic cancer, myelodysplastic syndrome (MDS), lung cancer, and gastric cancer, and/or fibrosis, preferably liver fibrosis and chronic kidney disease, in particular compounds that are more selective for TGFβR1.

The present invention provides a compound of the formula:

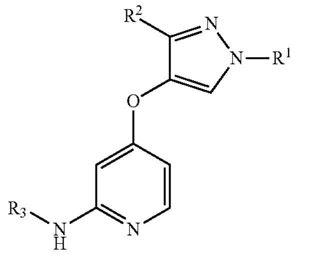

wherein:

$R^1$ is hydrogen, isopropyl, difluoromethyl, difluoroethyl, or cyclopropyl;

$R^2$ is ethyl, tert-butyl, pyridin-2-yl, tetrahydropyran-4-yl, tetrahydrofuran-3-yl, cyclopropyl, or cyclobutyl; and $R^3$ is carbamoylphenyl, pyridin-2-yl, (1-hydroxy-1-methylethyl)pyridinyl, 1-methyl-2-oxo-1H-pyridin-4-yl, 1-methylpyrazolyl, pyrazin-2-yl, 2-methoxypyrimidin-4-yl, 1-methyl-2-oxo-1H-pyrimidin-4-yl, pyridazin-3-yl, 6-chloropyridazin-3-yl, 6-methylpyridazin-3-yl, or 6-methoxypyridazin-3-yl;

or a pharmaceutically acceptable salt thereof.

The present invention also provides 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol or a pharmaceutically acceptable salt thereof.

The present invention also provides 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol-4-methylbenzenesulfonate.

The present invention also provides crystalline 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol 4-methylbenzenesulfonate. The present invention further provides crystalline 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol 4-methylbenzenesulfonate characterized by the X-ray powder diffraction pattern (Cu radiation, λ–1.54060 Å) comprising a peak at 17.8° with one or more peaks selected from the group consisting of 19.7°, 18.4°, and 22.0° (2θ±0.2°).

The present invention also provides a method of treating cancer, preferably colon cancer, melanoma, hepatocellular carcinoma (HCC), renal cancer, glioblastoma (GBM), pancreatic cancer, myelodysplastic syndrome (MDS), lung cancer, and gastric cancer, in a patient in need of such treatment comprising administering the patient an effective amount of a compound or salt of the present invention.

The present invention also provides a method of treating fibrosis, preferably liver fibrosis and chronic kidney disease, in a patient in need of such treatment comprising administering the patient an effective amount of a compound or salt of the present invention.

The present invention also provides a pharmaceutical composition comprising a compound or salt of the present invention, and one or more pharmaceutically acceptable excipients, carriers, or diluents.

This invention also provides a compound or salt of the present invention for use in therapy. Additionally, this invention provides a compound or salt of the present invention for use in the treatment of cancer, preferably colon cancer, melanoma, hepatocellular carcinoma (HCC), renal cancer, glioblastoma (GBM), pancreatic cancer, myelodysplastic syndrome (MDS), lung cancer, and gastric cancer and/or fibrosis, preferably liver fibrosis and chronic kidney disease. Furthermore, this invention provides the use of a compound or a salt of the present invention in the manufacture of a medicament for treating cancer, preferably colon cancer, melanoma, hepatocellular carcinoma (HCC), renal cancer, glioblastoma (GBM), pancreatic cancer, myelodysplastic syndrome (MDS), lung cancer, and gastric cancer and/or fibrosis, preferably liver fibrosis and chronic kidney disease The following paragraphs describe preferred classes of the present invention:

a) $R^1$ is difluoromethyl, difluoroethyl, or cyclopropyl;

b) $R^2$ is pyridin-2-yl, tetrahydropyran-4-yl, or cyclopropyl;

c) $R^3$ is carbamoylphenyl or (1-hydroxy-1-methylethyl)pyridinyl;

d) $R^1$ is cyclopropyl and $R^2$ is tetrahydropyran-4-yl;

e) $R^1$ is cyclopropyl and $R^2$ is cyclopropyl;

f) $R^1$ is difluoroethyl and $R^2$ is tetrahydropyran-4-yl;

g) $R^1$ is difluoromethyl and $R^2$ is pyridin-2-yl;

h) $R^1$ is cyclopropyl, $R^2$ is tetrahydropyran-4-yl, and $R^3$ is (1-hydroxy-1-methylethyl)pyridinyl;

i) $R^1$ is cyclopropyl, $R^2$ is cyclopropyl, and $R^3$ is (1-hydroxy-1-methylethyl)pyridinyl;

j) $R^1$ is difluoroethyl, $R^2$ is tetrahydropyran-4-yl, and $R^3$ is (1-hydroxy-1-methylethyl)pyridinyl; and k) $R^1$ is difluoromethyl, $R^2$ is pyridin-2-yl, and $R^3$ is carbamoylphenyl.

It will be understood by the skilled reader that free base forms of the compounds of the present invention are capable of forming salts and such salts are contemplated to be part of the present invention. The free base compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts," *Journal of Pharmaceutical Sciences*, Vol 66, No. 1, January 1977. It is understood by the skilled artisan that salt stoichiometry can be readily determined. See for example, D. Risley, et al., Simultaneous Determination of Positive and Negative Counterions Using a Hydrophilic Interaction Chromatography Method, *LCGC NORTH AMERICA*, Vol 24, No. 8, August 2006 pages 776-785.

Certain of the compounds of the present invention are crystalline. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present cases, a peak position variability of ±0.2 in 20 will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774 degrees 2-theta.

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques. The skilled artisan will appreciate that in some circumstances the elution order of enantiomers or diastereomers may be different due to different chromatographic columns and mobile phases.

The designation of "isomer 1" in a compound name represents that the corresponding intermediate or compound of the present invention is the first of two eluting enantiomers when a mixture of a pair of enantiomers is separated by chiral chromatography. The designation of "isomer 2" in a compound name represents that the corresponding intermediate or compound of the present invention that is the second of two eluting enantiomers when the mixture of a pair of enantiomers is separated by chiral chromatography.

Compounds of the present invention may be synthesized as illustrated in the following Schemes, where $R^1$, $R^2$, and $R^3$ are as previously defined.

Scheme 1: Synthesis of compounds of Formula I

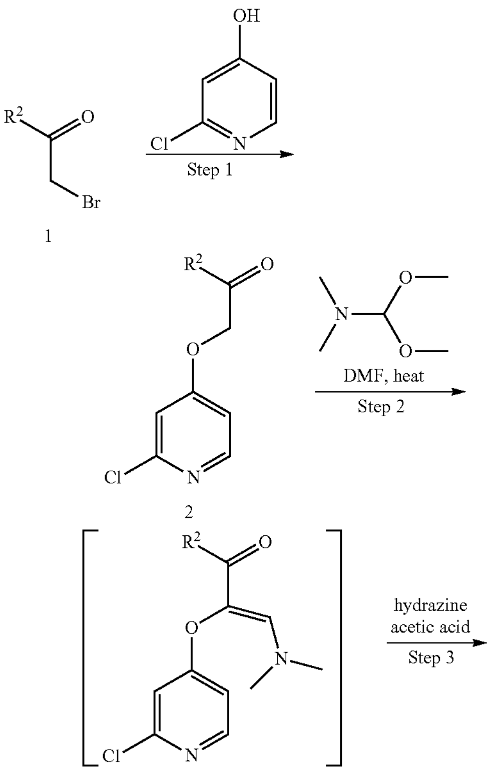

1

2

3

-continued

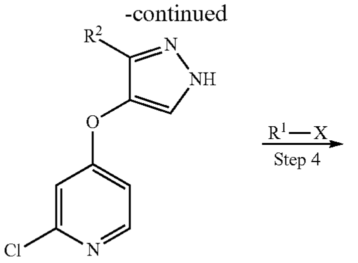

4

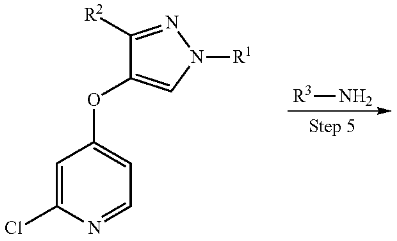

5

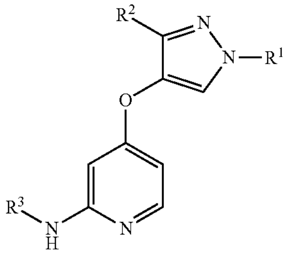

Formula I

Scheme 1 illustrates the general synthesis of compounds of Formula I. Compound 1 is reacted with 2-chloropyridin-4-ol in a suitable solvent such as dimethylformamide (DMF) or acetone with a suitable base such as cesium carbonate or potassium carbonate at room temperature or elevated temperature to afford Compound 2. Compound 2 is reacted with 1,1-dimethoxy-N,N-dimethyl-methanamine at elevated temperature to form Compound 3. Compound 3 can be purified or used without further purification to react with hydrazine in acetic acid to afford Compound 4. Compound 4 can react with a suitable alkylation reagent such as potassium alkyltrifluoroborate or alkyboronic acid under Chan-Lam coupling conditions to form Compound 5. More specifically, first heat a suspension of 2,2'-bipyridine and copper(II) acetate in a suitable solvent such as 1,2-dichloroethane to elevated temperature and purge with nitrogen, and then filter the reaction mixture and add the filtrate to a mixture of Compound 4, a suitable boronate such as potassium alkyltrifluoroborate or an alkylboronic acid, and a suitable base such as sodium carbonate in a suitable solvent such as 1,2-dichloroethane. Heat the reaction mixture to an elevated temperature to provide Compound 5. Compound 4 can also react with a suitable alkyl halide such as alkyl iodide, alkyl bromide or alkyl chloride with a suitable base such as sodium hydride in an appropriate solvent such as DMF or tetrahydrofuran (THF) to afford Compound 5. Compound 5 is reacted with a suitable amine under well-known Buchwald coupling conditions to provide a compound of Formula I. More specifically, Compound 5 is reacted with a suitable amine at elevated temperature in the presence of a suitable base such as cesium carbonate, a suitable ligand reagent such as 4,5-bis(diphenylphosphino)-9,9-dimethylxanthene, and a suitable catalyst such as palladium(II)acetate in an appropriate solvent such as 1,4-dioxane to afford a compound of Formula I.

Scheme 2: Synthesis of compounds of Formula I when $R^1$ is H

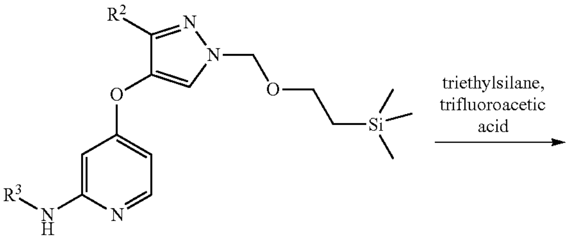

6

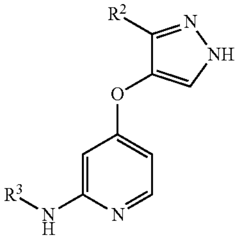

Formula I
$R^1$ is H

Scheme 2 illustrates the general synthesis of compounds of Formula I when $R^1$ is H. As illustrated in Step 4 of Scheme 1, when the alkylation reagent is 2-(trimethylsilyl)ethoxymethyl chloride, Compound 6 can be obtained by alkylation through Step 4 and Buchwald coupling reaction through Step 5. Compound 6 can react with triethylsilane in trifluoroacetic acid to provide a compound of Formula I in which $R^1$ is H. When $R^1$ is H, it is known to skilled artisans that a compound of Formula I can exist as a pair of tautomers in which the hydrogen can migrate between two nitrogens on the pyrazolyl ring.

Scheme 3: Synthesis of compounds of Formula I when $R^3$ is (carbamoyl)phenyl

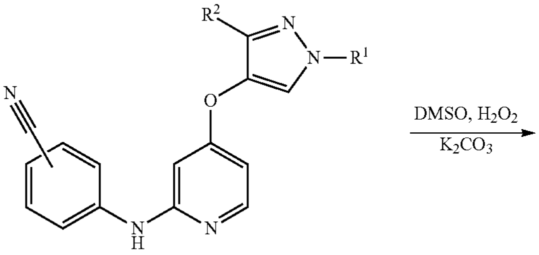

7

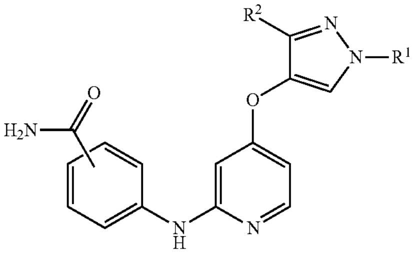

Formula I
$R^3$ is (carbamoyl)phenyl

Scheme 3 illustrates the general synthesis of compounds of Formula I when $R^3$ is a (carbamoyl)phenyl group. Compound 7 can be made by the method illustrated in Step 5 of Scheme 1 when $R^3$ is a suitably substituted benzonitrile. Compound 7 is reacted with hydrogen peroxide and a suitable base such as potassium carbonate in dimethyl sulfoxide (DMSO) to provide a compound of Formula I when $R^3$ is a (carbamoyl)phenyl group.

As used herein, the following terms have the meanings indicated: "ACN" refers to acetonitrile; "BSA" refers to bovine serum albumin; "DCM" refers to dichloromethane; "DMF" represents N,N-dimethylformamide; "DMSO" refers to dimethyl sulfoxide; "DTT" refers to dithiothreitol; "EDTA" refers to ethylenediaminetetraacetic acid; "EGTA" refers to ethylene glycol tetraacetic acid; "ELISA" refers to enzyme-linked immunosorbent assay; "EtOAc" refers to ethyl acetate; "EtOH" refers to ethanol; "FBS" refers to fetal bovine serum; "HEC" refers to hydroxyethylcellulose; "HPLC" refers to high performance liquid chromatography; "IVTI" refers to in vivo target inhibition; "MS" refers to mass spectroscopy; "MeOH" refers to methanol; "NMR" refers to nuclear magnetic resonance; "THF" refers to tetrahydrofuran; "TBS" refers to tris buffered saline; "TED" refers to threshold effective dose; "UVW" refers to ultraviolet wavelength, and "XRD" refers to X-ray diffraction.

Unless noted to the contrary, the compounds illustrated herein are named and numbered using either ACDLABS or Accelrys Draw 4.1.

Preparation 1

2-(4-Bromo-2-pyridyl)propan-2-ol

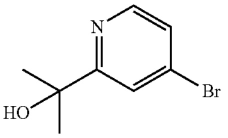

Equip a three-liter, three-neck round bottom flask with an addition funnel, a reflux condenser, a nitrogen inlet, and a temperature probe. Charge with methylmagnesium bromide (3.2M in 2-methyltetrahydrofuran, 239.07 mL, 765.01 mmol) and cool in an ice bath. To the addition funnel, add a solution of ethyl 4-bromopyridine-2-carboxylate (80.0 g, 347.73 mmol) in THF (800.0 mL). Add the solution dropwise to the methylmagnesium bromide solution while keeping the internal temperature below 25° C. Remove the cooling bath and allow stirring at 25° C. for 30 minutes. Cool the reaction mixture to 5° C. and quench carefully with the dropwise addition of aqueous hydrochloric acid solution (1M) while keeping the internal temperature below 30° C. Add additional aqueous hydrochloric acid solution (1M) until the mixture reaches a pH of around 7. Remove the cooling bath and dilute with ethyl acetate (EtOAc; 200 mL). Isolate the organic layer, dry over anhydrous sodium sulfate, filter through a CELITE® plug and rinse with EtOAc. Concentrate the filtrate to give an orange oil. Purify by using a silica gel plug eluting with hexane/EtOAc (3/1) to give the title compound (63.15 g; 84.0% yield) as a colorless oil. MS (m/z): 216/218 (M+1/M+3).

Prepare the following compound essentially by the method of Preparation 1.

TABLE 1

| Prep. No. | Chemical name | Structure | Physical data |
|---|---|---|---|
| 2 | 2-(5-Bromo-2-pyridyl)propan-2-ol | 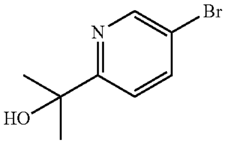 | MS (m/z): 216/218 (M + 1/M + 3) |

Preparation 3

2-(4-Amino-2-pyridyl)propan-2-ol

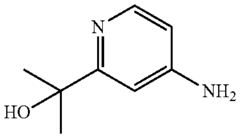

Charge a two-liter Parr reactor with a stirring bar, copper (powder mesh, 12.6 g, 198.6 mmol), 2-(4-bromo-2-pyridyl)propan-2-ol (63.1 g, 292.0 mmol) and ammonium hydroxide (28 wt/wt % in water, 757.2 mL). Stir the reaction mixture under open air for 30 minutes until it is dark blue. Remove the stirring bar, attach a mechanical stirring top, seal, and place on a stirrer. Heat the mixture to 100° C. (inner, heating bath at 120° C.) and stir overnight. Cool the reaction mixture to room temperature and add 2-methyltetrahydrofuran (600 mL). Filter through a CELITE® plug and rinse with 2-methyltetrahydrofuran. Isolate the organic layer and extract the aqueous layer with 2-methyltetrahydrofuran (200 mL). Combine the organic layers and dry over anhydrous sodium sulfate. Filter, concentrate and dry under vacuum overnight to give the title compound (31.3 g; 70.4% yield) as a yellow oil. MS (m/z): 153 (M+1).

Prepare the following compound essentially by the method of Preparation 3.

TABLE 2

| Prep. No. | Chemical name | Structure | Physical data |
|---|---|---|---|
| 4 | 2-(5-Amino-2-pyridyl) propan-2-ol | 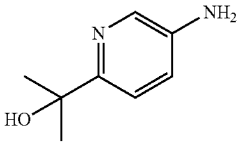 | MS (m/z): 153 (M + 1) |

Preparation 5

2-Bromo-1-tetrahydropyran-4-yl-ethanone

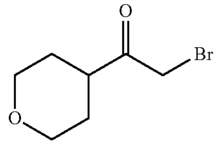

Method 1:

Add oxalyl chloride (28.69 mL, 330.73 mmol) dropwise to a mixture of tetrahydropyran-4-carboxylic acid (39.13 g, 300.67 mmol) in DCM (250 mL) and DMF (15 drops). Stir the mixture at room temperature for 2.5 hours under nitrogen. Concentrate under reduced pressure and dissolve the residue in DCM (250 mL). Add the resulting solution dropwise to (trimethylsilyl)diazomethane (2M in hexanes, 450 mL, 900.00 mmol) at −10° C. and stir the mixture at room temperature overnight. Cool the mixture to 0° C. and add hydrobromic acid (48 wt/wt % in water, 52 mL, 462.73 mmol) dropwise. Stir the mixture at room temperature for two hours. Cool the mixture to 0° C. and add hydrobromic acid (48 wt/wt % in water, 26 mL, 231.36 mmol) dropwise. Stir the mixture at room temperature for two hours. Add water (250 mL), DCM (250 mL) and isolate the organic layer. Extract the aqueous layer with DCM (2×250 mL). Combine the organic layers and wash with saturated aqueous sodium bicarbonate solution and saturated aqueous sodium chloride. Dry over anhydrous sodium sulfate and concentrate under reduced pressure to give the title compound (58.2 g; 93.48% yield) as a brown solid. $^1H$ NMR (300 MHz, $CDCl_3$) δ 4.00 (m, 2H), 3.95 (s, 2H), 3.45 (m, 2H), 2.98 (m, 1H), 1.78 (m, 4H).

Method 2:

Cool a solution of 1-tetrahydropyran-4-ylethanone (10 g, 78.02 mmol) in methanol (MeOH; 50 mL) to −10° C. Add bromine (4.01 mL, 78.02 mmol) dropwise. Stir the mixture at 0° C. for 45 minutes and then at 10° C. for 45 minutes. Add an aqueous solution of sulfuric acid (11M, 27.5 mL, 302.50 mmol) and stir the resulting mixture at room temperature overnight. Add water and extract with diethyl ether three times. Combine the organic layers. Wash with an aqueous solution of sodium bicarbonate and water. Dry over anhydrous sodium sulfate and concentrate under reduced pressure to give the title compound (12 g; 74.28% yield) as a white solid. $^1H$ NMR (400.13 MHz, $CDCl_3$) δ 4.00 (m, 2H), 3.95 (s, 2H), 3.45 (m, 2H), 2.98 (m, 1H), 1.78 (m, 4H).

Preparation 6

2-[(2-Chloro-4-pyridyl)oxy]-1-tetrahydropyran-4-yl-ethanone

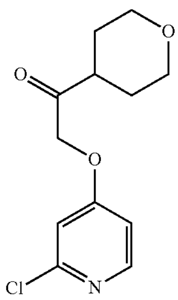 [SMILES: O=C(COc1ccnc(Cl)c1)C1CCOCC1]

Method 1:

Add a solution of 2-bromo-1-tetrahydropyran-4-yl-ethanone (24.35 g, 117.60 mmol) in DMF (50 mL) dropwise to a stirring mixture of 2-chloropyridin-4-ol (13.85 g, 106.91 mmol) and cesium carbonate (69.67 g, 213.82 mmol) in DMF (380 mL) at room temperature. Stir the resulting mixture at 90° C. for 2.5 hours. Cool to room temperature to give the crude mixture. Combine with a crude mixture of another 2.85 g (2-chloropyridin-4-ol) scale reaction run as indicated above. Dilute the combined mixture with water (200 mL) and EtOAc (300 mL). Isolate the organic layer and extract the aqueous layer with EtOAc (3×250 mL). Combine the organic layers and wash with water (100 mL) and saturate aqueous sodium chloride (100 mL). Dry over anhydrous sodium sulfate, filter and concentrate the filtrate under reduced pressure to give the title compound (29.32 g; 88.96% yield) as a brown oil. MS (m/z): 256 (M+1).

Method 2:

Add 2-bromo-1-tetrahydropyran-4-yl-ethanone (10.03 g, 48.42 mmol) and potassium carbonate (10.14 g, 72.62 mmol) to a solution of 2-chloropyridin-4-ol (6.40 g, 48.42 mmol) in acetone (150 mL) and stir the resulting mixture at room temperature overnight. Filter to remove the solid and wash the solid with DCM. Concentrate the filtrate under reduced pressure to give the title compound quantitatively. MS (m/z): 256 (M+1).

Prepare the following compounds essentially by the Method 2 of Preparation 6.

TABLE 3

| Prep. No. | Chemical name | Structure | Physical data MS (m/z): |
|---|---|---|---|
| 7 | 1-[(2-Chloro-4-pyridyl)oxy]butan-2-one | 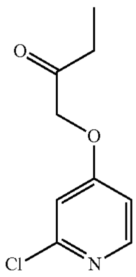 | 200 (M + 1) |
| 8 | 2-[(2-Chloro-4-pyridyl)oxy]-1-tetrahydrofuran-3-yl-ethanone | 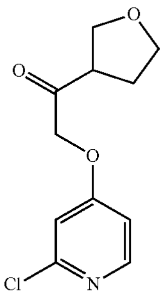 [SMILES: O=C(COc1ccnc(Cl)c1)C1CCOC1] | 242 (M + 1) |
| 9 | 1-[(2-Chloro-4-pyridyl)oxy]-3,3-dimethyl-butan-2-one | 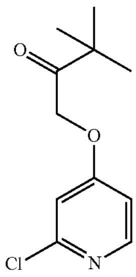 | 228 (M + 1) |

TABLE 3-continued

| Prep. No. | Chemical name | Structure | Physical data MS (m/z): |
|---|---|---|---|
| 10 | 2-[(2-Chloro-4-pyridyl)oxy]-1-cyclobutyl-ethanone | 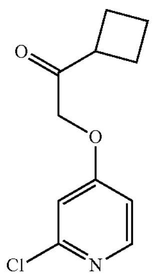 [SMILES: O=C(COc1ccnc(Cl)c1)C1CCC1] | 226 (M + 1) |
| 11 | 2-[(2-Chloro-4-pyridyl)oxy]-1-cyclopropyl-ethanone | 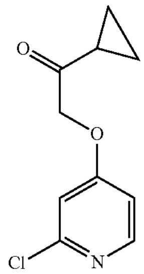 [SMILES: O=C(COc1ccnc(Cl)c1)C1CC1] | 212 (M + 1) |
| 12 | 2-[(2-Chloro-4-pyridyl)oxy]-1-(2-pyridyl)ethanone | 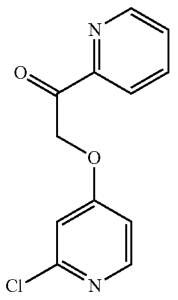 [SMILES: O=C(COc1ccnc(Cl)c1)c1ccccn1] | 249 (M + 1) |

Preparation 13

2-Chloro-4-[(3-tetrahydropyran-4-yl-1H-pyrazol-4-yl)oxy]pyridine

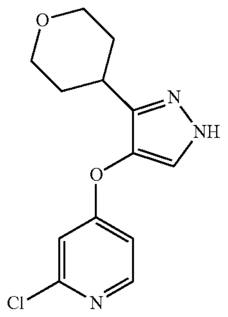 [SMILES: Clc1cc(Oc2c[nH]nc2C2CCOCC2)ccn1]

Stir a mixture of 2-[(2-chloro-4-pyridyl)oxy]-1-tetrahydropyran-4-yl-ethanone (29.3 g, 114.59 mmol) and 1,1-dimethoxy-N,N-dimethyl-methanamine (65 mL, 486.83 mmol) at 100° C. for two hours. Cool to room temperature, concentrate under reduced pressure and dissolve the residue in EtOAc (400 mL). Wash with water (100 mL) and saturated aqueous sodium chloride (100 mL). Dry over anhydrous sodium sulfate and concentrate under reduced pressure to give a brown solid. Dissolve in acetic acid (350 mL) and cool to 0° C. Add hydrazine monohydrate (16.8 mL, 345.66 mmol) and stir at room temperature overnight under nitrogen. Pour the mixture into an ice/water mixture (250 mL) and extract with EtOAc (4×200 mL). Combine the organic layers and wash with water (200 mL), saturated aqueous sodium bicarbonate solution (100 mL) and saturated aqueous sodium chloride (100 mL). Dry over anhydrous sodium sulfate, filter and concentrate the filtrate under reduced pressure to give a brown oil. Purify the brown oil by using a silica gel plug eluting with EtOAc. Combine the appropriate fractions and concentrate under reduced pressure. Dry under vacuum to give the title compound (24.43 g; 76.22% yield) as a yellow solid. MS (m/z): 280 (M+1).

Prepare the following compounds essentially by the method of Preparation 13.

TABLE 4

| Prep. No. | Chemical name | Structure | Physical data MS (m/z): |
|---|---|---|---|
| 14 | 2-Chloro-4-[(3-ethyl-1H-pyrazol-4-yl)oxy]pyridine | 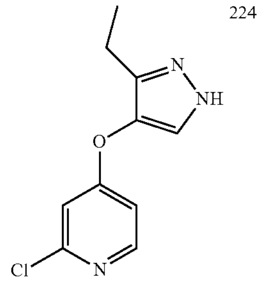 | 224 (M + 1) |
| 15 | 2-Chloro-4-[(3-tetrahydrofuran-3-yl-1H-pyrazol-4-yl)oxy] pyridine | 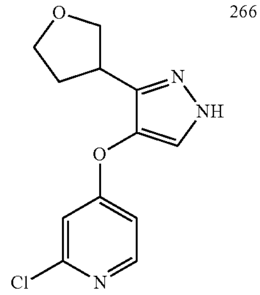 | 266 (M + 1) |
| 16 | 4-[(3-Tert-butyl-1H-pyrazol-4-yl)oxy]-2-chloro-pyridine | 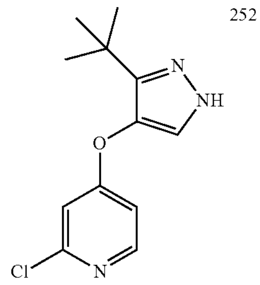 | 252 (M + 1) |

TABLE 4-continued

| Prep. No. | Chemical name | Structure | Physical data MS (m/z): |
|---|---|---|---|
| 17 | 2-Chloro-4-[(3-cyclobutyl-1H-pyrazol-4-yl)oxy]pyridine | 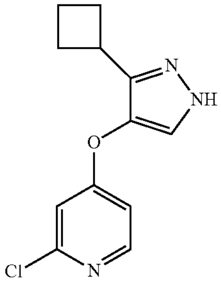 [SMILES: Clc1cc(Oc2c[nH]nc2C2CCC2)ccn1] | 250 (M + 1) |
| 18 | 2-Chloro-4-[(3-cyclopropyl-1H-pyrazol-4-yl)oxy]pyridine | 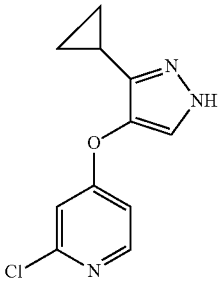 [SMILES: Clc1cc(Oc2c[nH]nc2C2CC2)ccn1] | 236 (M + 1) |
| 19 | 2-Chloro-4-[[3-(2-pyridyl)-1H-pyrazol-4-yl]oxy]pyridine | 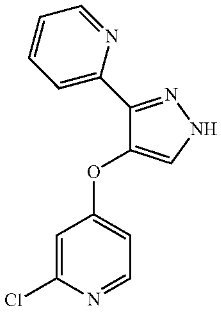 [SMILES: Clc1cc(Oc2c[nH]nc2-c2ccccn2)ccn1] | 273 (M + 1) |

Preparation 20

2-Chloro-4-(1-cyclopropyl-3-tetrahydropyran-4-yl-pyrazol-4-yl)oxy-pyridine

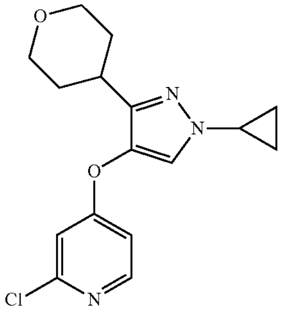 [SMILES: Clc1cc(Oc2cn(C3CC3)nc2C2CCOCC2)ccn1]

Method 1:

Reflux a mixture of 2,2'-bipyridine (13.73 g, 87.90 mmol) and copper(II)acetate (15.97 g, 87.90 mmol) in 1,2-dichloroethane (244.3 mL) at 75° C. for 25 minutes and then cool to room temperature. Add a solution of 2-chloro-4-[(3-tetrahydropyran-4-yl-1H-pyrazol-4-yl)oxy]pyridine (24.43 g, 79.91 mmol) in 1,2-dichloroethane (335.30 mL), then add cyclopropylboronic acid (13.73 g, 159.82 mmol) and sodium carbonate (16.94 g, 159.82 mmol). Heat the reaction mixture at 75° C. for two hours under an oxygen atmosphere and cool to room temperature. Dilute with EtOAc (200 mL), filter through a silica gel plug and rinse with EtOAc (250 mL). Wash the filtrate with water (200 mL) and saturated aqueous sodium chloride (200 mL). Dry over anhydrous sodium sulfate, filter and concentrate the filtrate under reduced pressure and dry the residue under vacuum at room temperature overnight. Purify by silica gel column chromatography with 6-27% EtOAc in DCM to give the title compound (20.75 g; 81.2% yield) as a yellow solid. MS (m/z): 320 (M+1).

Method 2:

Heat a suspension of 2,2'-bipyridine (28.8 g, 56.5 mmol) and copper(II)acetate (8.2 g, 45.2 mmol) in 1,2-dichloroethane (50 mL) to 70° C. and purge with nitrogen for 3 minutes. Filter and add the filtrate to a mixture of 2-chloro-4-[(3-tetrahydropyran-4-yl-1H-pyrazol-4-yl)oxy]pyridine (8 g, 22.6 mmol), potassium cyclopropyl(trifluoro)borate (6.7 g, 45.2 mmol) and sodium carbonate (4.8 g, 45.2 mmol) in 1,2-dichloroethane (50 mL). Heat the reaction mixture at 70° C. for four days. Cool to room temperature. Filter and rinse with DCM. Wash the filtrate with saturated aqueous ammonium chloride solution and saturated aqueous sodium bicarbonate solution. Dry over anhydrous sodium sulfate, filter and concentrate the filtrate under reduced pressure. Purify by silica gel column chromatography with 1-10% MeOH in DCM to give the title compound (6.0 g; 82.2% yield). MS (m/z): 320 (M+1).

Prepare the following compounds essentially by Method 1 of Preparation 20. Alteration in work up procedure is indicated.

TABLE 5

| Prep. No. | Chemical name | Structure | Physical data MS (m/z): | Comments |
|---|---|---|---|---|
| 21 | 2-Chloro-4-(3-cyclobutyl-1-cyclopropyl-pyrazol-4-yl)oxy-pyridine | 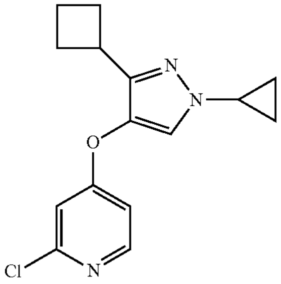 [SMILES: Clc1cc(Oc2cn(C3CC3)nc2C2CCC2)ccn1] | 290 (M + 1) | |
| 22 | 2-Chloro-4-(1,3-dicyclopropylpyrazol-4-yl)oxy-pyridine | 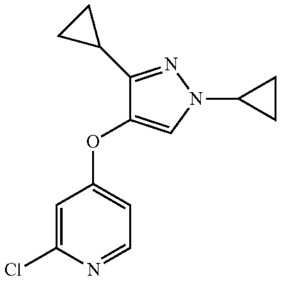 [SMILES: Clc1cc(Oc2cn(C3CC3)nc2C2CC2)ccn1] | 276 (M + 1) | |
| 23 | 2-Chloro-4-[1-cyclopropyl-3-(2-pyridyl)pyrazol-4-yl]oxy-pyridine | 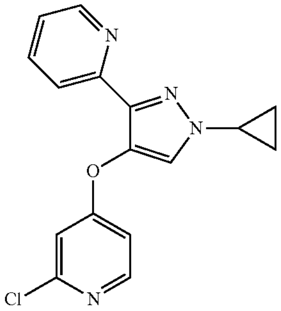 [SMILES: Clc1cc(Oc2cn(C3CC3)nc2-c2ccccn2)ccn1] | 313 (M + 1) | Use 23% ammonia hydroxide in water to quench the reaction. |

Prepare the following compounds essentially by Method 2 of Preparation 20.

TABLE 6

| Prep. No. | Chemical name | Structure | Physical data MS (m/z): |
|---|---|---|---|
| 24 | 2-Chloro-4-(1-cyclopropyl-3-ethyl-pyrazol-4-yl)oxy-pyridine | 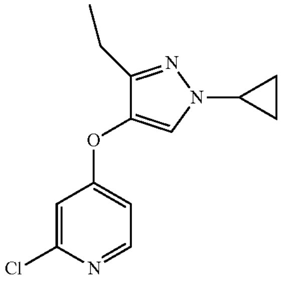 [SMILES: CCc1nn(C2CC2)cc1Oc1ccnc(Cl)c1] | 264 (M + 1) |

TABLE 6-continued

| Prep. No. | Chemical name | Structure | Physical data MS (m/z): |
|---|---|---|---|
| 25 | 2-Chloro-4-(1-cyclopropyl-3-tetrahydrofuran-3-yl-pyrazol-4-yl)oxy-pyridine | 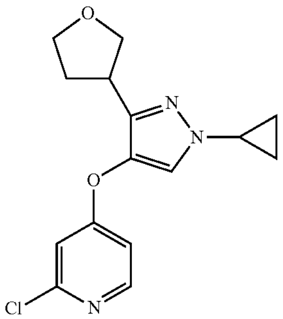 [SMILES: Clc1cc(Oc2cn(C3CC3)nc2C2CCOC2)ccn1] | 306 (M + 1) |
| 26 | 4-(3-Tert-butyl-1-cyclopropyl-pyrazol-4-yl)oxy-2-chloro-pyridine | 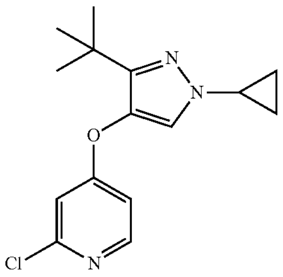 [SMILES: CC(C)(C)c1nn(C2CC2)cc1Oc1ccnc(Cl)c1] | 292 (M + 1) |

Preparation 27

2-Chloro-4-(1-cyclopropyl-3-tetrahydrofuran-3-yl-pyrazol-4-yl)oxy-pyridine, isomer 1

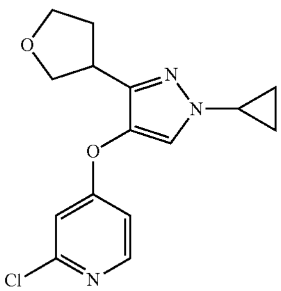 [SMILES: Clc1cc(Oc2cn(C3CC3)nc2C2CCOC2)ccn1]

Purify the racemic mixture of 2-chloro-4-(1-cyclopropyl-3-tetrahydrofuran-3-yl-pyrazol-4-yl)oxy-pyridine (Preparation 25) with chiral chromatography to afford the first eluting enantiomer as the title compound. MS (m/z): 306 (M+1).

Purification condition: CHIRALPAK® IC; Mobile Phase: 20% ethanol (EtOH) in carbon dioxide; Flow rate: 300 g/min; UVW: 240 nm; Retention time: 2.44 minutes.

Preparation 28

2-Chloro-4-(1-cyclopropyl-3-tetrahydrofuran-3-yl-pyrazol-4-yl)oxy-pyridine, isomer 2

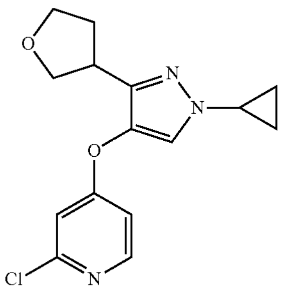 [SMILES: Clc1cc(Oc2cn(C3CC3)nc2C2CCOC2)ccn1]

Purify the racemic mixture of 2-chloro-4-(1-cyclopropyl-3-tetrahydrofuran-3-yl-pyrazol-4-yl)oxy-pyridine (Preparation 25) with chiral chromatography to afford the second eluting enantiomer as the title compound. MS (m/z): 306 (M+1).

Purification condition: CHIRALPAK® IC; Mobile Phase: 20% EtOH in carbon dioxide; Flow rate: 300 g/minute; UVW: 240 nm; Retention time: 2.93 minutes.

Preparation 29

2-Chloro-4-[1-(difluoromethyl)-3-(2-pyridyl)pyrazol-4-yl]oxy-pyridine

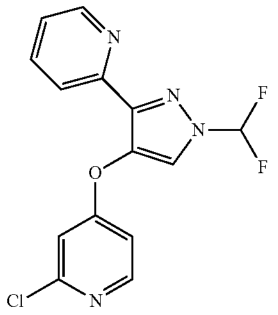 [SMILES: FC(F)n1cc(Oc2ccnc(Cl)c2)c(-c2ccccn2)n1]

Cool a solution of 2-chloro-4-[[3-(2-pyridyl)-1H-pyrazol-4-yl]oxy]pyridine (2.0 g, 7.33 mmol) in DMF (73.34 mL) in an ice bath and add sodium hydride (60% in mineral oil, 880.02 mg, 22.00 mmol) portionwise. Stir the mixture at 0° C. for 10 minutes, allow it to warm to room temperature and stir for 10 minutes. Add difluoroiodomethane (10 wt % in THF, 27.19 mL, 36.67 mmol) and stir the reaction mixture at 45° C. overnight. Cool to room temperature and dilute with EtOAc. Wash with 5% aqueous lithium chloride solution first and then wash with saturated aqueous sodium chloride. Dry over anhydrous sodium sulfate, filter and concentrate the filtrate under reduced pressure. Purify the residue by silica gel column chromatography with 0-50% EtOAc in DCM. Combine the appropriate fractions and concentrate under reduced pressure. Purify the residue by silica gel column chromatography with 0-10% EtOAc in DCM to give the title compound (1.56 g; 65.9% yield). MS (m/z): 323 (M+1).

Prepare the following compounds essentially by the method of Preparation 29. Alterations in solvent, base, and/or reaction temperature are indicated.

TABLE 7

| Prep. No. | Chemical name | Structure | Physical data | Comments |
|---|---|---|---|---|
| 30 | 2-Chloro-4-[3-cyclopropyl-1-difluoromethyl)pyrazol-4-yl]oxy-pyridine | 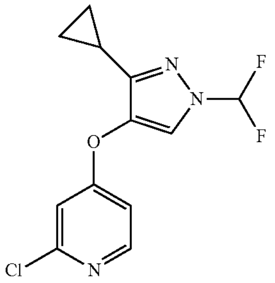 [SMILES: FC(F)n1cc(Oc2ccnc(Cl)c2)c(C2CC2)n1] | MS (m/z): 286 (M + 1) | THF, potassium tert-butoxide, |
| 31 | 2-Chloro-4-[1-(difluoromethyl)-3-tetrahydropyran-4-yl-pyrazol-4-yl]oxy-pyridine | 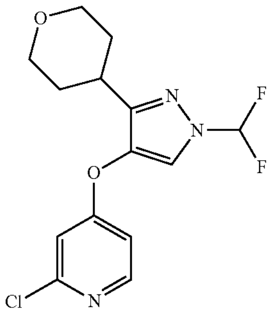 [SMILES: FC(F)n1cc(Oc2ccnc(Cl)c2)c(C2CCOCC2)n1] | $^1$H NMR (399.83 MHz, DMSO-$d_6$) δ 8.42 (s, 1H), 8.30 (d, J = 5.6 Hz, 1H), 7.71 (t, J = 59.2 Hz, 1H), 7.15 (d, J = 2.4 Hz, 1H), 7.04 (dd, J = 2.4 Hz, J = 5.6 Hz, 1H, 3.81 (m, 2H), 3.33 (m, 2H), 2.80 (m, 1H), 1.64 (m, 4H). | |
| 32 | 2-Chloro-4-[1-(difluoromethyl)-3-tetrahydrofuran-3-yl-pyrazol-4-yl]oxy-pyridine | 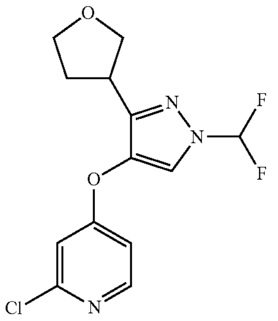 [SMILES: FC(F)n1cc(Oc2ccnc(Cl)c2)c(C2CCOC2)n1] | $^1$H NMR (399.83 MHz, DMSO-$d_6$) δ 8.46 (s, 1H), 8.30 (d, J = 5.6 Hz, 1H), 7.71 (t, J = 59.2 Hz, 1H), 7.16 (d, J = 2.4 Hz, 1H), 7.05 (dd, J = 2.4 Hz, J = 5.6 Hz, 1H), 3.89 (t, J = 6.0 Hz, 1H), 3.68 (m, 3H), 3.26 (m, 1H), 2.12 (m, 1H), 1.99 (m, 1H). | |

TABLE 7-continued

| Prep. No. | Chemical name | Structure | Physical data | Comments |
|---|---|---|---|---|
| 33 | 2-Chloro-4-[3-cyclobutyl-1-difluoromethyl)pyrazol-4-yl]oxy-pyridine | 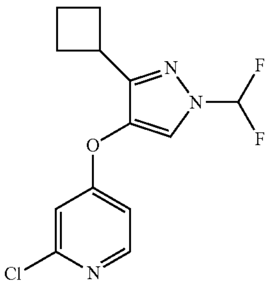 [SMILES: FC(F)n1cc(Oc2ccnc(Cl)c2)c(C2CCC2)n1] | MS (m/z): 300 (M + 1) | |
| 34 | 2-Chloro-4-[1-isopropyl-3-(2-pyridyl)pyrazol-4-yl]oxy-pyridine | 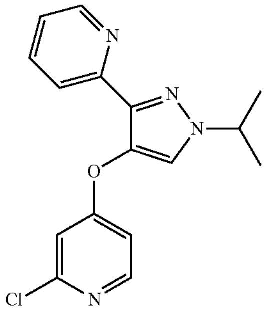 [SMILES: CC(C)n1cc(Oc2ccnc(Cl)c2)c(-c2ccccn2)n1] | MS (m/z): 315 (M + 1) | THF, potassium tert-butoxide, reflux overnight |
| 35 | 2-Chloro-4-(3-cyclopropyl-1-isopropyl-pyrazol-4-yl)oxy-pyridine | 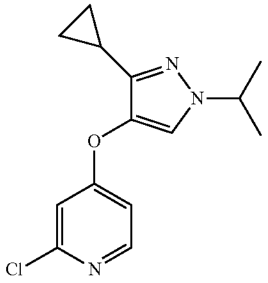 [SMILES: CC(C)n1cc(Oc2ccnc(Cl)c2)c(C2CC2)n1] | MS (m/z): 278 (M + 1) | room temperature |
| 36 | 2-Chloro-4-(1-isopropyl-3-tetrahydropyran-4-yl-pyrazol-4-yl)oxy-pyridine | 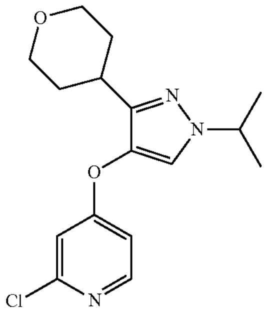 [SMILES: CC(C)n1cc(Oc2ccnc(Cl)c2)c(C2CCOCC2)n1] | MS (m/z): 322 (M + 1) | room temperature |
| 37 | 2-Chloro-4-(3-cyclobutyl-1-isopropyl-pyrazol-4-yl)oxy-pyridine | 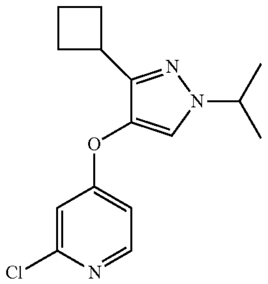 [SMILES: CC(C)n1cc(Oc2ccnc(Cl)c2)c(C2CCC2)n1] | MS (m/z): 292 (M + 1) | room temperature |

TABLE 7-continued

| Prep. No. | Chemical name | Structure | Physical data | Comments |
|---|---|---|---|---|
| 38 | 2-Chloro-4-[1-(2,2-difluoroethyl)-3-(2-pyridyl)pyrazol-4-yl]oxy-pyridine | 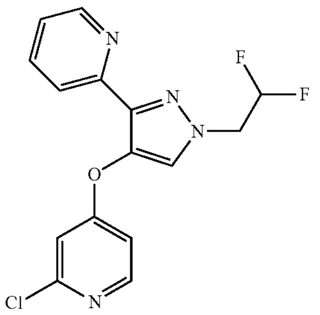 [SMILES: FC(F)Cn1cc(Oc2ccnc(Cl)c2)c(-c2ccccn2)n1] | MS (m/z): 337 (M + 1) | THF, potassium tert-butoxide, 50° C. |
| 39 | 2-Chloro-4-[3-cyclopropyl-1-(2,2-difluoroethyl)pyrazol-4-yl]oxy-pyridine | 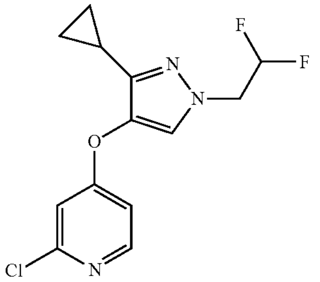 [SMILES: FC(F)Cn1cc(Oc2ccnc(Cl)c2)c(C2CC2)n1] | MS (m/z): 300 (M + 1) | Cesium carbonate, 50° C. |
| 40 | 2-Chloro-4-[1-(2,2-difluoroethyl)-3-tetrahydropyran-4-yl-pyrazol-4-yl]oxy-pyridine | 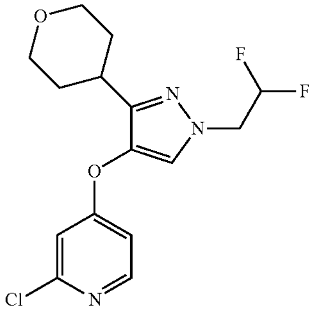 [SMILES: FC(F)Cn1cc(Oc2ccnc(Cl)c2)c(C2CCOCC2)n1] | MS (m/z): 344 (M + 1) | Cesium carbonate, 50° C. |

Preparation 41

2-Chloro-4-{[3-(pyridin-2-yl)-1-{[2-(trimethylsilyl)ethoxy]methyl}-1H-pyrazol-4-yl]oxy}pyridine

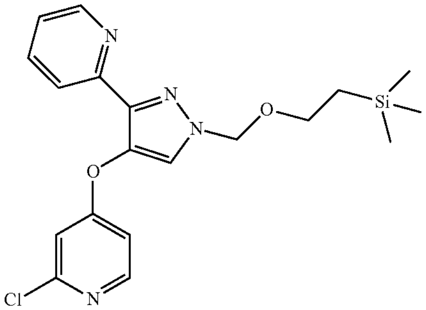 [SMILES: C[Si](C)(C)CCOCn1cc(Oc2ccnc(Cl)c2)c(-c2ccccn2)n1]

Add sodium hydride (60% suspension in mineral oil, 484 mg, 12.10 mmol) to a solution of 2-chloro-4-[[3-(2-pyridyl)-1H-pyrazol-4-yl]oxy]pyridine (3.0 g, 11.00 mmol) in THF (110 mL) at 0° C. Stir for 15 minutes at 0° C. and add 2-(trimethylsilyl)ethoxymethyl chloride (2.02 g, 12.10 mmol). Stir the reaction mixture at room temperature overnight. Concentrate the mixture. Partition the residue between DCM and water. Isolate the organic layer and dry over sodium sulfate. Filter the mixture and concentrate the filtrate under reduced pressure. Purify the residue by silica gel column chromatography with 0-30% EtOAc in hexane to give the title compound (3.64 g; 82.1% yield). MS (m/z): 403 (M+1).

Preparation 42

4-[[4-(1-Cyclopropyl-3-tetrahydropyran-4-yl-pyrazol-4-yl)oxy-2-pyridyl]amino]benzonitrile

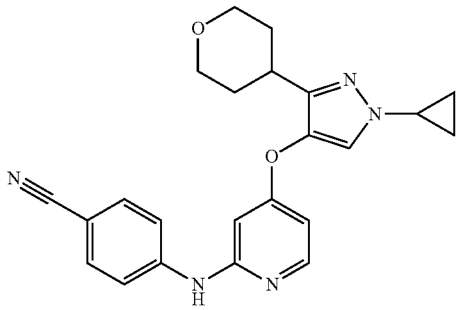 [SMILES: N#Cc1ccc(Nc2cc(Oc3cn(C4CC4)nc3C3CCOCC3)ccn2)cc1]

Purge a solution of 2-chloro-4-(1-cyclopropyl-3-tetrahydropyran-4-yl-pyrazol-4-yl)oxy-pyridine (400 mg, 1.2 mmol), p-aminobenzonitrile (219.9 mg, 1.9 mmol), cesium carbonate (568.5 mg, 1.7 mmol), 4,5-bis(diphenylphosphino)-9,9-dimethylxanthene (134.6 mg, 0.23 mmol) in 1,4-dioxane (15 mL) with nitrogen for five minutes. Treat the resulting mixture with palladium(II)acetate (26.1 mg, 0.12 mmol) and purge with nitrogen for 5 minutes. Close the vial and stir at 100° C. for two hours then 80° C. over the weekend. Cool to room temperature, filter through a CELITE® plug and wash with 5% MeOH in DCM. Concentrate the filtrate to give the title compound (467 mg; 100% yield). MS (m/z): 402 (M+1).

Prepare the following compounds essentially by the method of Preparation 42. Alterations in catalyst, and/or solvent are indicated.

TABLE 8

| Prep. No. | Chemical name | Structure | Physical data MS (m/z): | Comments |
|---|---|---|---|---|
| 43 | 2-[5-[[4-[3-(2-Pyridyl)-1-(2-trimethylsilylethoxy-methyl)pyrazol-4-yl]oxy-2-pyridyl]amino]-2-pyridyl]propan-2-ol | 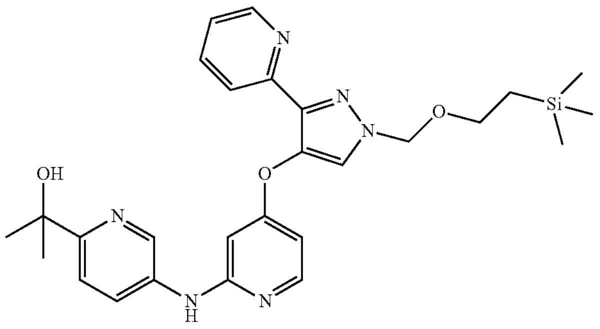 [SMILES: CC(C)(O)c1ccc(Nc2cc(Oc3cn(COCC[Si](C)(C)C)nc3-c3ccccn3)ccn2)cn1] | 519 (M + 1) | Tris(dibenzyl-ideneacetone)-dipalladium(0), toluene |
| 44 | Methyl 4-[[4-(3-cyclopropyl-1-isopropyl-pyrazol-4-yl)oxy-2-pyridyl]amino]pyridine-2-carboxylate | 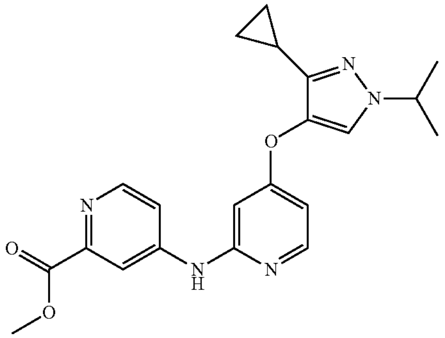 [SMILES: COC(=O)c1cc(Nc2cc(Oc3cn(C(C)C)nc3C3CC3)ccn2)ccn1] | 394 (M + 1) | Tris(dibenzyl-ideneacetone)-dipalladium(0), toluene |
| 45 | 4-[[4-[1-Isopropyl-3-(2-pyridyl)pyrazol-4-yl]oxy-2-pyridyl]amino] benzonitrile | 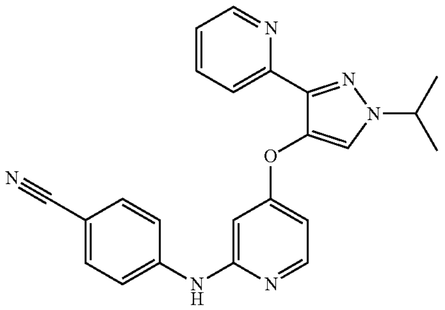 [SMILES: CC(C)n1cc(Oc2ccnc(Nc3ccc(C#N)cc3)c2)c(-c2ccccn2)n1] | 397 (M + 1) | |
| 46 | 3-[[4-(1-Cyclopropyl-3- tetrahydropyran-4-yl-pyrazol-4-yl)oxy-2-pyridyl]amino] benzonitrile | 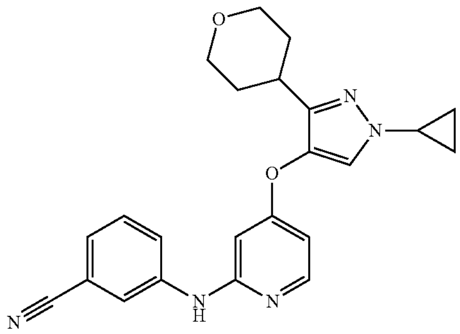 [SMILES: N#Cc1cccc(Nc2cc(Oc3cn(C4CC4)nc3C3CCOCC3)ccn2)c1] | 402 (M + 1) | |

TABLE 8-continued

| Prep. No. | Chemical name | Structure | Physical data MS (m/z): | Comments |
|---|---|---|---|---|
| 47 | 4- [[4-(1-Cyclopropyl-3-ethyl-pyrazol-4-yl)oxy-2-pyridyl]amino] benzonitrile | 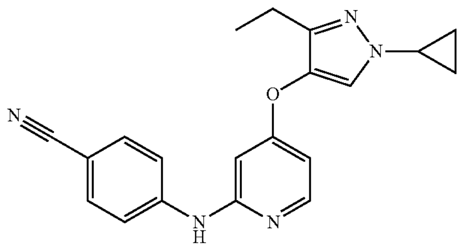 [SMILES: CCc1nn(C2CC2)cc1Oc1ccnc(Nc2ccc(C#N)cc2)c1] | 346 (M + 1) | |
| 48 | 4-[[4-[1-(Difluoromethyl)-3-tetrahydropyran-4-yl-pyrazol-4-yl]oxy-2-pyridyl]amino] benzonilrile | 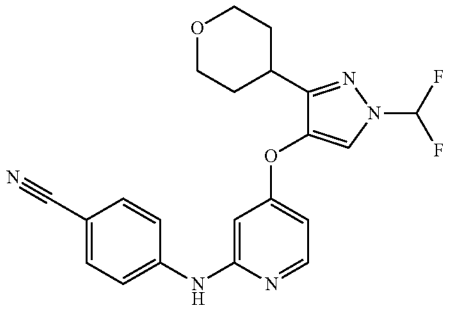 [SMILES: N#Cc1ccc(Nc2cc(Oc3cn(C(F)F)nc3C3CCOCC3)ccn2)cc1] | 412 (M + 1) | |
| 49 | N-[4-[1-(Difluoromethyl)-3-tetrahydrofuran-3-yl-pyrazol-4-yl]oxy-2-pyridyl]pyridazin-3-amine | 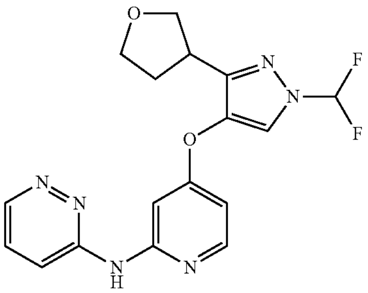 [SMILES: FC(F)n1cc(Oc2ccnc(Nc3cccnn3)c2)c(C2CCOC2)n1] | 375 (M + l) | Tris(dibenzyl-ideneacetone)-dipalladium(0) |
| 50 | 2-[4-[[4-(1-Cyclopropyl-3-tetrahydrofuran-3-yl-pyrazol-4-yl)oxy-2-pyridyl]amino]-2-pyridyl]propan-2-ol | 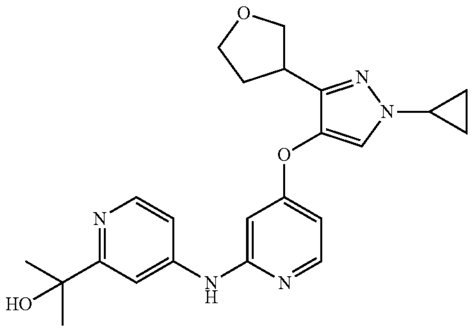 [SMILES: CC(C)(O)c1cc(Nc2cc(Oc3cn(C4CC4)nc3C3CCOC3)ccn2)ccn1] | 422 (M + 1) | |
| 51 | 4-[[4-[3-Cyclobutyl-1-(difluoromethyl)pyrazol-4-yl]oxy-2-pyridyl]amino] benzonitrile | 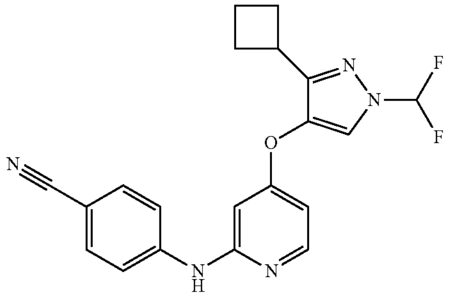 [SMILES: N#Cc1ccc(Nc2cc(Oc3cn(C(F)F)nc3C3CCC3)ccn2)cc1] | 382 (M + 1) | |

TABLE 8-continued

| Prep. No. | Chemical name | Structure | Physical data MS (m/z): | Comments |
|---|---|---|---|---|
| 52 | 3-[[4-[1-(Difluoromethyl)-3-(2-pyridyl)pyrazol-4-yl]oxy-2-pyridyl]amino] benzonitrile | 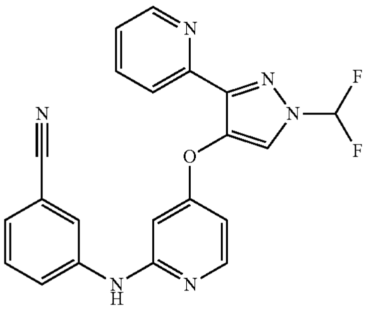 [SMILES: N#Cc1cccc(Nc2cc(Oc3cn(C(F)F)nc3-c3ccccn3)ccn2)c1] | 405 (M + 1) | |
| 53 | 4-[[4-(1,3-Dicyclopropylpyrazol-4-yl)oxy-2-pyridyl]amino] benzonitrile | 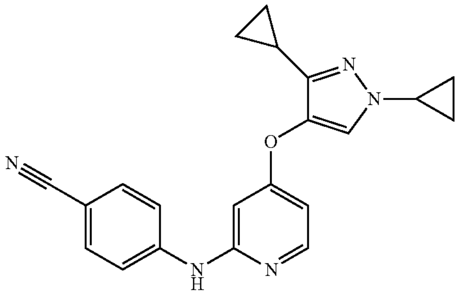 [SMILES: N#Cc1ccc(Nc2cc(Oc3cn(C4CC4)nc3C3CC3)ccn2)cc1] | 358 (M + 1) | |

EXAMPLE 1

2-{4-[(4-{[1-Cyclopropyl-3-(tetrahydro-2H-pyran-4-yl)-1H-pyrazol-4-yl]oxy}pyridin-2-yl)amino]pyridin-2-yl}propan-2-ol

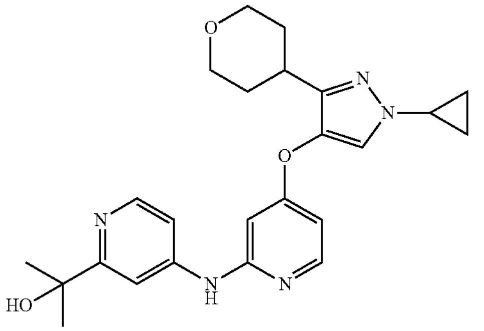 [SMILES: CC(C)(O)c1cc(Nc2cc(Oc3cn(C4CC4)nc3C3CCOCC3)ccn2)ccn1]

Method 1:

Purge a solution of 2-chloro-4-(1-cyclopropyl-3-tetrahydropyran-4-yl-pyrazol-4-yl)oxy-pyridine (45.6 g, 142.6 mmol), 2-(4-amino-2-pyridyl)propan-2-ol (26.0 g, 171.1 mmol) and sodium phenate (26.5 g, 228.2 mmol) in 1,4-dioxane (456 mL) with nitrogen for 20 minutes. Treat the resulting mixture with 4,5-bis(diphenylphosphino)-9,9-dimethylxanthene (8.25 g, 14.3 mmol) and bis(dibenzylideneacetone)palladium (4.10 g, 7.13 mmol). Reflux for 21 hours. Cool the reaction to room temperature and stir overnight. Filter through a CELITE® plug and wash with DCM (500 mL). Concentrate the filtrate onto silica gel. Purify by silica gel column chromatography with 0-10% MeOH in EtOAc. Concentrate appropriate fractions and dry under vacuum overnight to give the title compound (58.7 g; 91.7% yield). MS (m/z): 436 (M+1). Several batches of the product are produced using the above method. Dissolve the combined batches of the title compounds (92.4 g) in EtOH (1 L). Treat the solution with QUADRASIL® MP (100 g, 1.0-1.5 mmol/g) and agitate at 60° C. for one hour. Cool to room temperature and filter to remove the solids. Concentrate to remove the solvent. Dissolve the residue in EtOH (500 mL) while heating at 100° C. Then cool the mixture slowly to room temperature and add water (500 mL) slowly. Cool the mixture to 5° C. while stirring. Collect the solid by filtration and dry under vacuum at 45° C. overnight to give the title compound (81.8 g). MS (m/z): 436 (M+1).

Method 2:

Dissolve 2-chloro-4-(1-cyclopropyl-3-tetrahydropyran-4-yl-pyrazol-4-yl)oxy-pyridine (400 mg, 1.2 mmol) in 1,4-dioxane (15 mL) in a vial. Add 2-(4-amino-2-pyridyl)propan-2-ol (266.5 mg, 1.6 mmol), cesium carbonate (568.5 mg, 1.7 mmol), 4,5-bis(diphenylphosphino)-9,9-dimethylxanthene (134.6 mg, 0.23 mmol) and purge with nitrogen for 5 minutes. Add palladium(II)acetate (26.1 mg, 0.12 mmol) and purge with nitrogen for 5 minutes. Seal the vial and stir at 100° C. overnight. Cool the reaction to room temperature, filter through a CELITE® plug and wash with 5% MeOH in DCM. Concentrate and purify by reverse phase chromatography (Redisep Rf Gold High Performance C18 Reverse Phase Column, 0-100% formic acid/acetonitrile (ACN) in formic acid/water). Concentrate appropriate fractions and dry under vacuum to give the title compound (341 mg; 67.3% yield). MS (m/z): 436 (M+1).

Prepare the following compounds essentially by the Method 2 of Example 1. Alterations in base, catalyst, ligand, and/or solvent are indicated.

TABLE 9

| Ex. No. | Chemical name | Structure | Physical data MS (m/z): | Comments |
|---|---|---|---|---|
| 2 | N-(4-{[1-(Difluoromethyl)-3-(pyridin-2-yl)-1H-pyrazol-4-yl]oxy}pyridin-2-yl)-6-methoxypyridazin-3-amine | 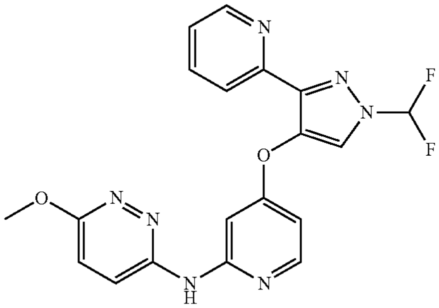 [SMILES: COc1ccc(Nc2cc(Oc3cn(C(F)F)nc3-c3ccccn3)ccn2)nn1] | 412 (M + 1) | bis(dibenzylidene-acetone)palladium |
| 3 | N-(4-{[1-(Difluoromethyl)-3-(pyridin-2-yl)-1H-pyrazol-4-yl]oxy}pyridin-2-yl)-2-methoxypyrimidin-4-amine | 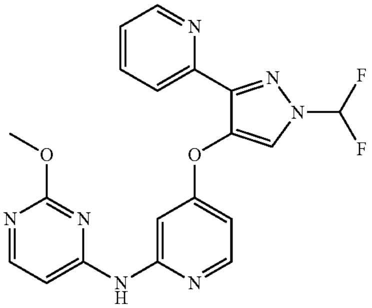 [SMILES: COc1nccc(Nc2cc(Oc3cn(C(F)F)nc3-c3ccccn3)ccn2)n1] | 412 (M + 1) | bis(dibenzylidene-acetone)palladium |
| 4 | 4-{[1-(Difluoromethyl)-3-(pyridin-2-yl)-1H-pyrazol-4-yl]oxy}-N-(pyridin-2-yl)pyridin-2-amine | 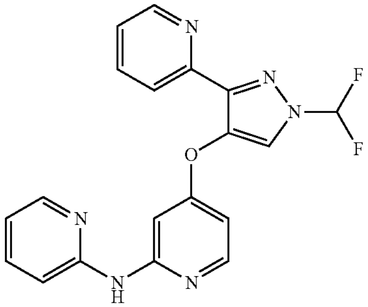 [SMILES: FC(F)n1cc(Oc2ccnc(Nc3ccccn3)c2)c(-c2ccccn2)n1] | 381 (M + 1) | |
| 5 | 6-Chloro-N-(4-{[1-cyclopropyl-3-(tetrahydro-2H-pyran-4-yl)-1H-pyrazol)-4-yl]oxy}pyridin-2-yl)pyridazin-3-amine | 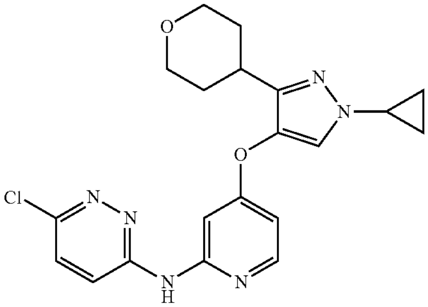 [SMILES: Clc1ccc(Nc2cc(Oc3cn(C4CC4)nc3C3CCOCC3)ccn2)nn1] | 413 (M + 1) | |
| 6 | N-(4-{[1-Cyclopropyl-3-(tetrahydro-2H-pyran-4-yl)-1H-pyrazol-4-yl]oxy}pyridin-2-yl)-6-methoxypyridazin-3-amine | 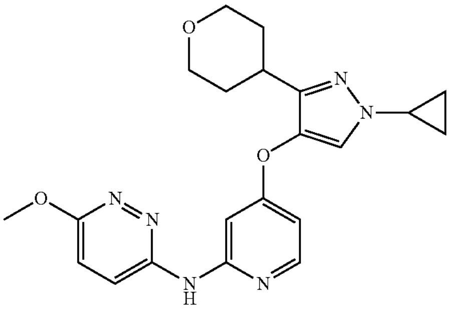 [SMILES: COc1ccc(Nc2cc(Oc3cn(C4CC4)nc3C3CCOCC3)ccn2)nn1] | 409 (M + 1) | |

TABLE 9-continued

| Ex. No. | Chemical name | Structure | Physical data MS (m/z): | Comments |
|---|---|---|---|---|
| 7 | N-(4-{[1-Cyclopropyl-3-(tetrahydro-2H-pyran-4-yl)-1H-pyrazol-4-yl]oxy}pyridin-2-yl)-6-methylpyridazin-3-amine | 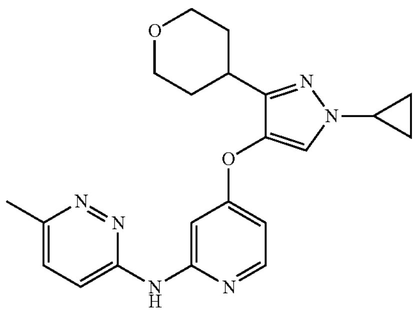 [SMILES: Cc1ccc(Nc2cc(Oc3cn(C4CC4)nc3C3CCOCC3)ccn2)nn1] | 393 (M + 1) | |
| 8 | N-(4-{[1-Cyclopropyl-3-(tetrahydro-2H-pyran-4-yl)-1H-pyrazol-4-yl]oxy}pyridin-2-yl)pyrazin-2-amine | 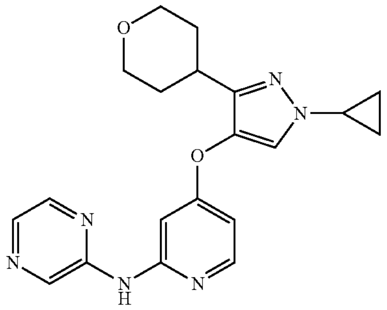 [SMILES: c1cnc(Nc2cc(Oc3cn(C4CC4)nc3C3CCOCC3)ccn2)cn1] | 379 (M + 1) | |
| 9 | 2-{2-[(4-{[1-Cyclopropyl-3-(tetrahydro-2H-pyran-4-yl)-1H-pyrazol-4-yl]oxy}pyridin-2-yl)amino]pyridin-4-yl}propan-2-ol | 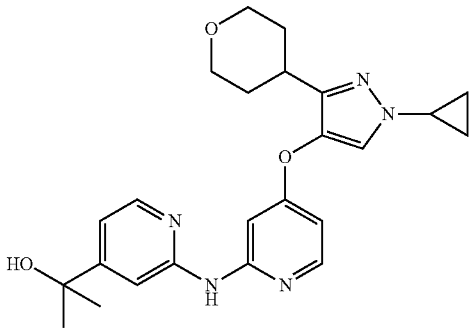 [SMILES: CC(C)(O)c1ccnc(Nc2cc(Oc3cn(C4CC4)nc3C3CCOCC3)ccn2)c1] | 436 (M + 1) | |
| 10 | 4-{[1-(2,2-Difluoroethyl)-3-(pyridin-2-yl)-1H-pyrazol-4-yl]oxy}-N-(1-methyl-1H-pyrazol-3-yl)pyridin-2-amine | 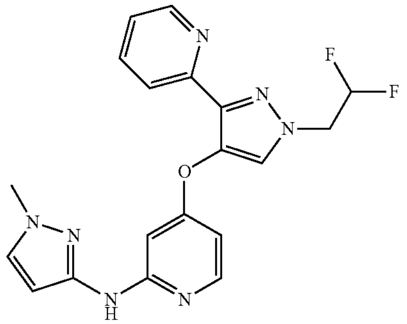 [SMILES: Cn1ccc(Nc2cc(Oc3cn(CC(F)F)nc3-c3ccccn3)ccn2)n1] | 398 (M + 1) | sodium phenate, bis(dibenzylidene-acetone)palladium |

TABLE 9-continued

| Ex. No. | Chemical name | Structure | Physical data MS (m/z): | Comments |
|---|---|---|---|---|
| 11 | 4-{[1-(2,2-Difluoroethyl)-3-(pyridin-2-yl)-1H-pyrazol-4-yl]oxy}-N-(1-methyl-1H-pyrazol-4-yl)pyridin-2-amine | 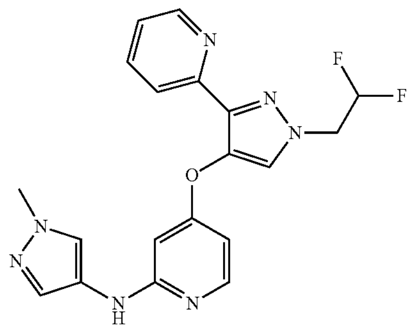 [SMILES: Cn1cc(Nc2cc(Oc3cn(CC(F)F)nc3-c3ccccn3)ccn2)cn1] | 398 (M + 1) | sodium phenate, bis(dibenzylidene-acetone)palladium |
| 12 | 2-{5-[(4-{[1-(2,2-Difluoroethyl)-3-(pyridin-2-yl)-1H-pyrazol-4-yl]oxy}pyridin-2-yl)amino]pyridin-2-yl}propan-2-ol | 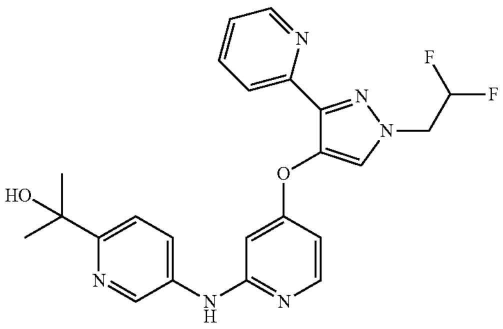 [SMILES: CC(C)(O)c1ccc(Nc2cc(Oc3cn(CC(F)F)nc3-c3ccccn3)ccn2)cn1] | 453 (M + 1) | sodium phenate, bis(dibenzylidene-acetone)palladium |
| 13 | 4-{[1-(Difluoromethyl)-3-(pyridin-2-yl)-1H-pyrazol-4-yl]oxy}-N-(1-methyl-1H-pyrazol-5-yl)pyridin-2-amine | 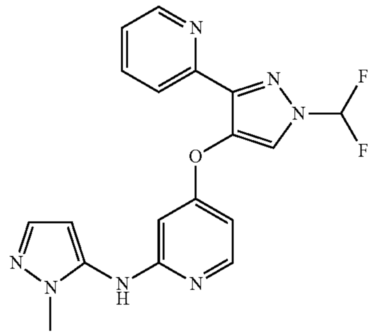 [SMILES: Cn1nccc1Nc1cc(Oc2cn(C(F)F)nc2-c2ccccn2)ccn1] | 384 (M + 1) | bis(dibenzylidene-acetone)palladium |
| 14 | 4-{[1-(Difluoromethyl)-3-(pyridin-2-yl)-1H-pyrazol-4-yl]oxy}-N-(1-methyl-1H-pyrazol-4-yl)pyridin-2-amine | 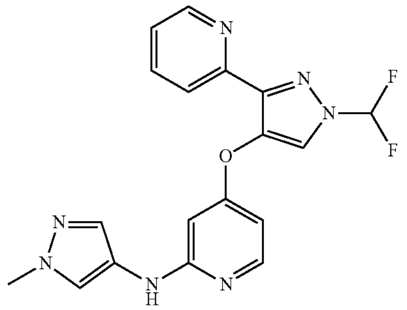 [SMILES: Cn1cc(Nc2cc(Oc3cn(C(F)F)nc3-c3ccccn3)ccn2)cn1] | 384 (M + 1) | bis(dibenzylidene-acetone)palladium |

TABLE 9-continued

| Ex. No. | Chemical name | Structure | Physical data MS (m/z): | Comments |
|---|---|---|---|---|
| 15 | N-(4-{[1-(Difluoromethyl)-3-(pyridin-2-yl)-1H-pyrazol-4-yl]oxy}pyridin-2-yl)pyridazin-3-amine | 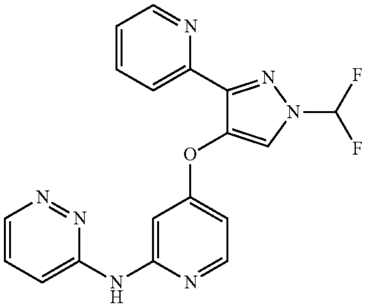 [SMILES: FC(F)n1cc(Oc2ccnc(Nc3cccnn3)c2)c(-c2ccccn2)n1] | 382 (M + 1) | bis(dibenzylidene-acetone)palladium |
| 16 | 2-{6-[(4-{[1-Cyclopropyl-3-(pyridin-2-yl)-1H-pyrazol-4-yl]oxy}pyridin-2-yl)amino]pyridin-3-yl}propan-2-ol | 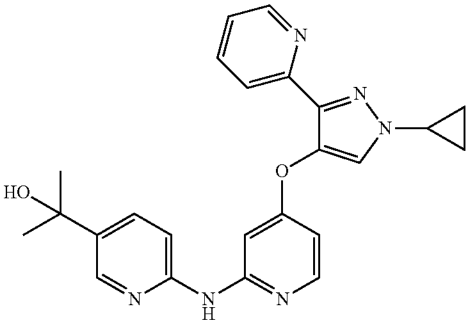 [SMILES: CC(C)(O)c1ccc(Nc2cc(Oc3cn(C4CC4)nc3-c3ccccn3)ccn2)nc1] | 429 (M + 1) | |
| 17 | 2-{5-[(4-{[1-Cyclopropyl-3-(pyridin-2-yl)-1H-pyrazol-4-yl]oxy}pyridin-2-yl)amino]pyridin-2-yl}propan-2-ol | 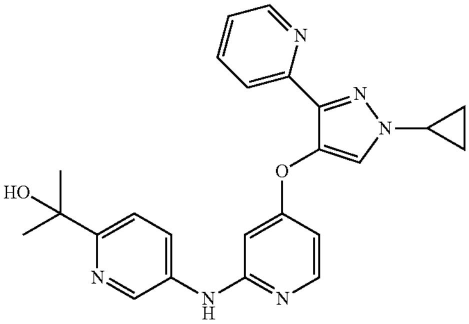 [SMILES: CC(C)(O)c1ccc(Nc2cc(Oc3cn(C4CC4)nc3-c3ccccn3)ccn2)cn1] | 429 (M + 1) | |
| 18 | 2-{4-[(4-{[1-Cyclopropyl-3-(pyridin-2-yl)-1H-pyrazol-4-yl]oxy}pyridin-2-yl)amino]pyridin-2-yl}propan-2-ol | 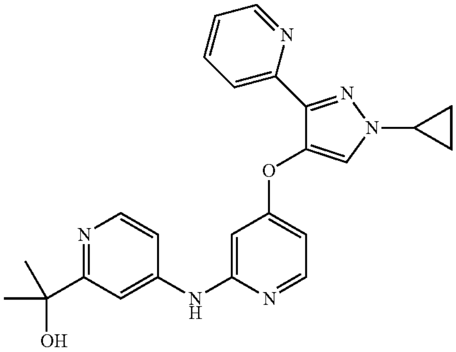 [SMILES: CC(C)(O)c1cc(Nc2cc(Oc3cn(C4CC4)nc3-c3ccccn3)ccn2)ccn1] | 429 (M + 1) | |

TABLE 9-continued

| Ex. No. | Chemical name | Structure | Physical data MS (m/z): | Comments |
|---|---|---|---|---|
| 19 | 2-{6-[(4-{[1-(Propan-2-yl)-3-(pyridin-2-yl)-1H-pyrazol-4-yl]oxy}pyridin-2-yl)amino]pyridin-3-yl}propan-2-ol | 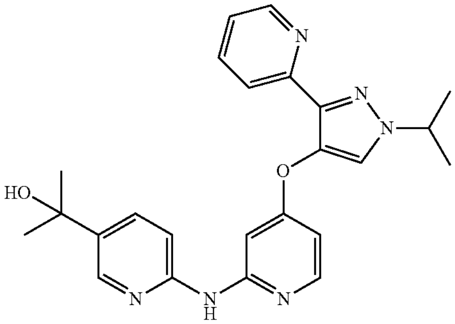 [SMILES: CC(C)n1cc(Oc2ccnc(Nc3ccc(C(C)(C)O)cn3)c2)c(-c2ccccn2)n1] | 431 (M + 1) | sodium phenate, bis(dibenzylidene-acetone)palladium |
| 20 | 1-Methyl-4-[(4-{[1-(propan-2-yl)-3-(pyridin-2-yl)-1H-pyrazol-4-yl]oxy}pyridin-2-yl)amino]pyridin-2(1H)-one | 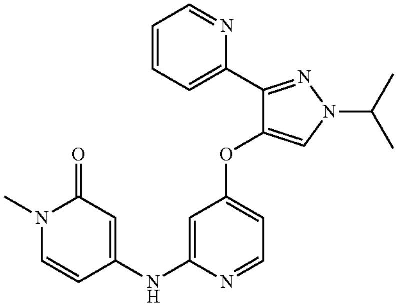 [SMILES: CC(C)n1cc(Oc2ccnc(Nc3ccn(C)c(=O)c3)c2)c(-c2ccccn2)n1] | 403 (M + 1) | |
| 21 | N-(4-{[1-(Propan-2-yl)-3-(pyridin-2-yl)-1H-pyrazol-4-yl]oxy}pyridin-2-yl)pyridazin-3-amine | 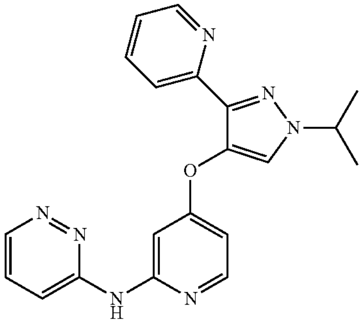 [SMILES: CC(C)n1cc(Oc2ccnc(Nc3cccnn3)c2)c(-c2ccccn2)n1] | 374 (M + 1) | |
| 22 | N-{4-[(3-Tert-butyl-1-cyclopropyl-1H-pyrazol-4-yl)oxy]pyridin-2-yl}pyridazin-3-amine | 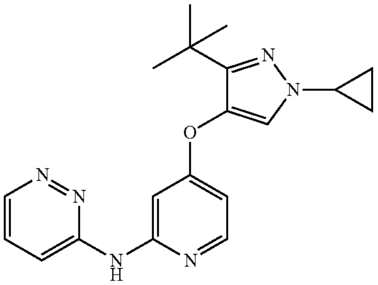 [SMILES: CC(C)(C)c1nn(C2CC2)cc1Oc1ccnc(Nc2cccnn2)c1] | 351 (M + 1) | |
| 23 | 2-[5-({4-[(3-Tert-butyl-1-cyclopropyl-1H-pyrazol-4-yl)oxy]pyridin-2-yl}amino)pyridin-2-yl]propan-2-ol | 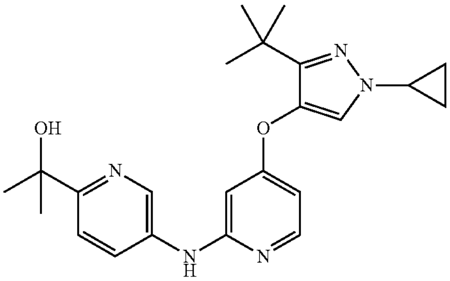 [SMILES: CC(C)(C)c1nn(C2CC2)cc1Oc1ccnc(Nc2ccc(C(C)(C)O)nc2)c1] | 408 (M + 1) | |

TABLE 9-continued

| Ex. No. | Chemical name | Structure | Physical data MS (m/z): | Comments |
|---|---|---|---|---|
| 24 | 2-[4-({4-[(3-Terl-butyl-1-cyclopropyl-1H-pyrazol-4-yl)oxy]pyridin-2-yl}amino)pyridin-2-yl]propan-2-ol | 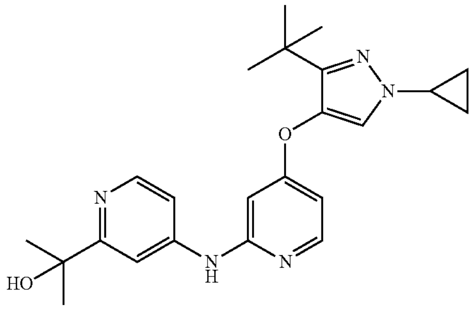 [SMILES: CC(C)(C)c1nn(C2CC2)cc1Oc1ccnc(Nc2ccnc(C(C)(C)O)c2)c1] | 408 (M + 1) | |
| 25 | 2-[4-({4-[(1-Cyclopropyl-3-ethyl-1H-pyrazol-4-yl)oxy]pyridin-2-yl}amino)pyridin-2-yl]propan-2-ol | 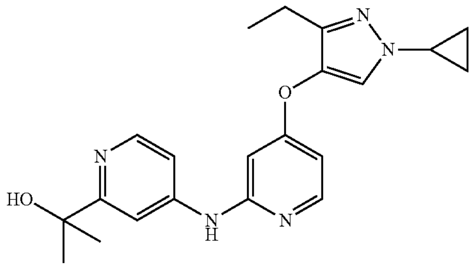 [SMILES: CCc1nn(C2CC2)cc1Oc1ccnc(Nc2ccnc(C(C)(C)O)c2)c1] | 380 (M + 1) | |
| 26 | 4-{[3-Cyclopropyl-1-(difluoromethyl)-1H-pyrazol-4-yl]oxy}-N-(1-methyl-1H-pyrazol-4-yl)pyridin-2-amine | 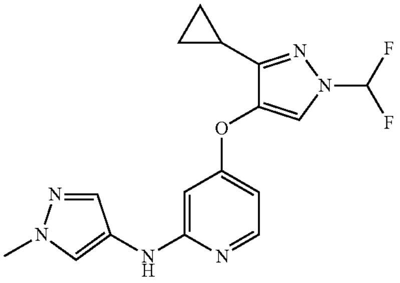 [SMILES: Cn1cc(Nc2cc(Oc3cn(C(F)F)nc3C3CC3)ccn2)cn1] | 347 (M + 1) | bis(dibenzylidene-acetone)palladium |
| 27 | 2-{4-[(4-{[3-Cyclopropyl-1-(2,2-difluoroethyl)-1H-pyrazol-4-yl]oxy}pyridin-2-yl)amino]pyridin-2-yl}propan-2-ol | 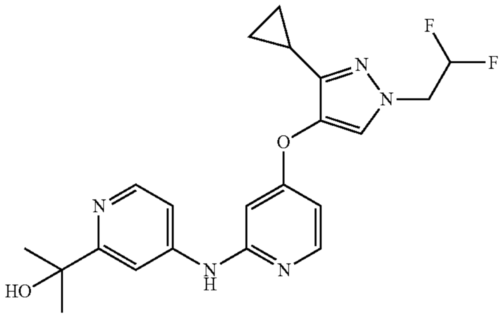 [SMILES: CC(C)(O)c1cc(Nc2cc(Oc3cn(CC(F)F)nc3C3CC3)ccn2)ccn1] | 416 (M + 1) | sodium phenate, bis(dibenzylidene-acetone)palladium |
| 28 | N-(4-{[3-Cyclopropyl-1-(difluoromethyl)-1H-pyrazol-4-yl]oxy}pyridin-2-yl)pyridazin-3-amine | 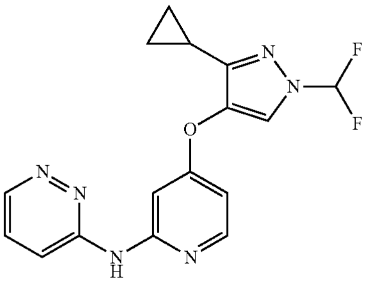 [SMILES: FC(F)n1cc(Oc2ccnc(Nc3cccnn3)c2)c(C2CC2)n1] | 345 (M + 1) | bis(dibenzylidene-acetone)palladium |

TABLE 9-continued

| Ex. No. | Chemical name | Structure | Physical data MS (m/z): | Comments |
|---|---|---|---|---|
| 29 | 4-({4-[(1,3-Dicyclopropyl-1H-pyrazol-4-yl)oxy]pyridin-2-yl}amino)-1-methylpyrimidin-2(1H)-one | 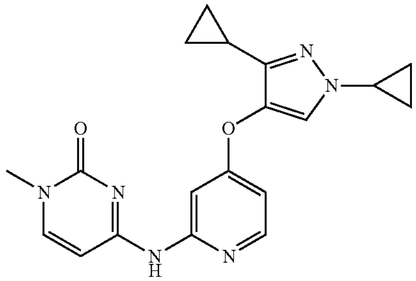 [SMILES: Cn1ccc(Nc2cc(Oc3cn(C4CC4)nc3C3CC3)ccn2)nc1=O] | 365 (M + 1) | |
| 30 | 4-[(1,3-Dicyclopropyl-1H-pyrazol-4-yl)oxy]-N-(1-methyl-1H-pyrazol-3-yl)pyridin-2-amine | 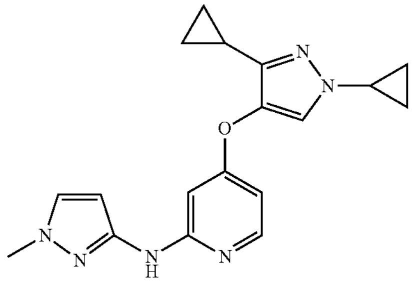 [SMILES: Cn1ccc(Nc2cc(Oc3cn(C4CC4)nc3C3CC3)ccn2)n1] | 337 (M + 1) | |
| 31 | 2-[6-({4-[(1,3-Dicyclopropyl-1H-pyrazol-4-yl)oxy]pyridin-2-yl}amino)pyridin-3-yl]propan-2-ol | 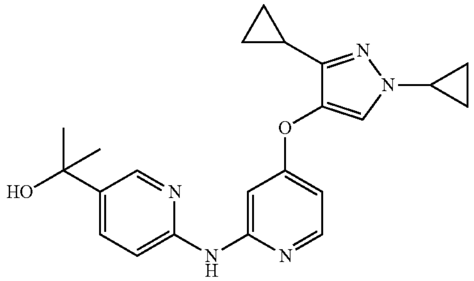 [SMILES: CC(C)(O)c1ccc(Nc2cc(Oc3cn(C4CC4)nc3C3CC3)ccn2)nc1] | 392 (M + 1) | sodium phenate, bis(dibenzylideneacetone)palladium |
| 32 | 4-[(1,3-Dicyclopropyl-1H-pyrazol-4-yl)oxy]-N-(1-methyl-1H-pyrazol-4-yl)pyridin-2-amine | 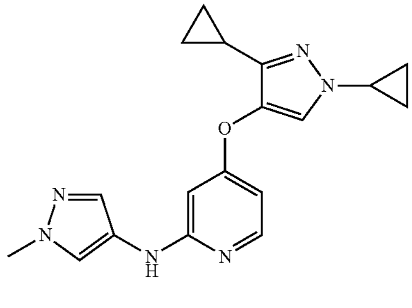 [SMILES: Cn1cc(Nc2cc(Oc3cn(C4CC4)nc3C3CC3)ccn2)cn1] | 337 (M + 1) | sodium phenate, bis(dibenzylideneacetone)palladium |
| 33 | 4-({4-[(1,3-Dicyclopropyl-1H-pyrazol-4-yl)oxy]pyridin-2-yl}amino)-1-methylpyridin-2(1H)-one | 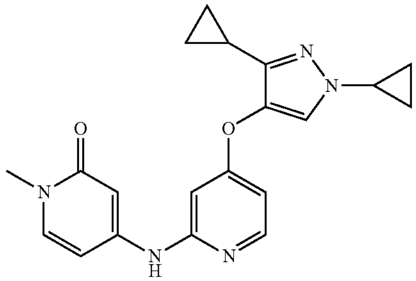 [SMILES: Cn1ccc(Nc2cc(Oc3cn(C4CC4)nc3C3CC3)ccn2)cc1=O] | 364 (M + 1) | bis(dibenzylideneacetone)palladium, toluene/N-methylpyrrolidone |

TABLE 9-continued

| Ex. No. | Chemical name | Structure | Physical data MS (m/z): | Comments |
|---|---|---|---|---|
| 34 | N-{4-[(1,3-Dicyclopropyl-1H-pyrazol-4-yl)oxy]pyridin-2-yl}pyridazin-3-amine | 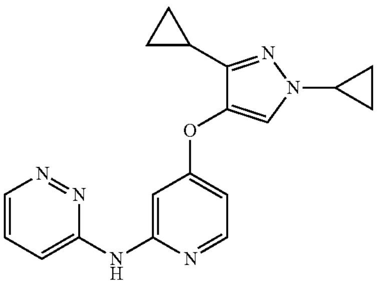 [SMILES: c1cnnc(Nc2cc(Oc3cn(C4CC4)nc3C3CC3)ccn2)c1] | 335 (M + 1) | |
| 35 | 2-{4-[(4-{(1-(2,2-Difluoroethyl)-3-(tetrahydro-2H-pyran-4-yl)-1H-pyrazol-4-yl]oxy}pyridin-2-yl)amino]pyridin-2-yl}propan-2-ol | 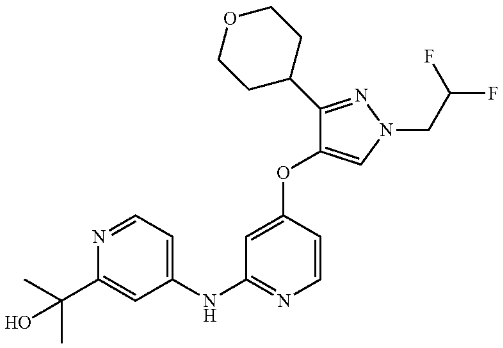 [SMILES: CC(C)(O)c1cc(Nc2cc(Oc3cn(CC(F)F)nc3C3CCOCC3)ccn2)ccn1] | 460 (M + 1) | sodium phenate, bis(dibenzylidene-acetone)palladium |
| 36 | N-(4-{[1-(Difluoromethyl)-3-(tetrahydro-2H-pyran-4-yl)-1H-pyrazol-4-yl]oxy}pyridin-2-yl)pyridazin-3-amine | 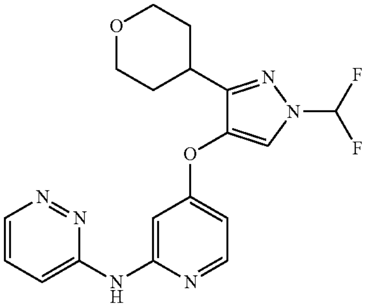 [SMILES: FC(F)n1cc(Oc2ccnc(Nc3cccnn3)c2)c(C2CCOCC2)n1] | 389 (M + 1) | bis(dibenzylidene-acetone)palladium |
| 37 | 4-{[1-Cyclopropyl-3-(tetrahydro-2H-pyran-4-yl)-1H-pyrazol-4-yl]oxy}-N-(1-methyl-1H-pyrazol-5-yl)pyridin-2-amine | 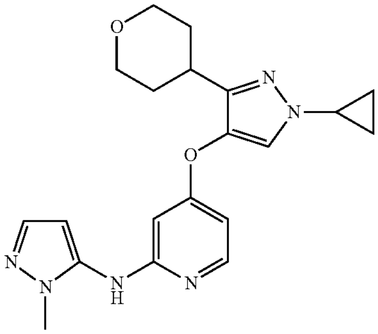 [SMILES: Cn1nccc1Nc1cc(Oc2cn(C3CC3)nc2C2CCOCC2)ccn1] | 381 (M + 1) | bis(dibenzylidene-acetone)palladium |

TABLE 9-continued

| Ex. No. | Chemical name | Structure | Physical data MS (m/z): | Comments |
|---|---|---|---|---|
| 38 | 4-{[l-Cyclopropyl-3-(tetrahydro-2H-pyran-4-yl)-1H-pyrazol-4-yl]oxy}-N-(1-methyl-1H-pyrazol-4-yl)pyridin-2-amine | 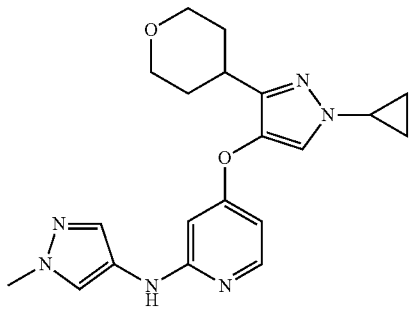 [SMILES: Cn1cc(Nc2cc(Oc3cn(C4CC4)nc3C3CCOCC3)ccn2)cn1] | 381 (M + 1) | bis(dibenzylidene-acetone)palladium |
| 39 | 4-[(4-{[1-Cyclopropyl-3-(tetrahydro-2H-pyran-4-yl)-1H-pyrazol-4-yl]oxy}pyridin-2-yl)amino]-1-methylpyridin-2(1H)-one | 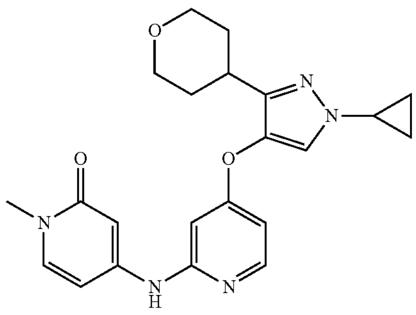 [SMILES: Cn1ccc(Nc2cc(Oc3cn(C4CC4)nc3C3CCOCC3)ccn2)cc1=O] | 408 (M + 1) | |
| 40 | N-(4-{[1-Cyclopropyl-3-(tetrahydro-2H-pyran-4-yl)-1H-pyrazol-4-yl]oxy}pyridin-2-yl)pyridazin-3-amine | 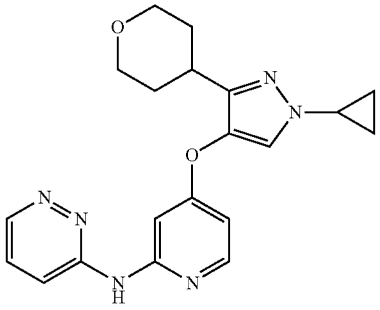 [SMILES: c1cnnc(Nc2cc(Oc3cn(C4CC4)nc3C3CCOCC3)ccn2)c1] | 379 (M + 1) | |
| 41 | 4-[(4-{[1-Cyclopropyl-3-(tetrahydrofuran-3-yl)-1H-pyrazol-4-yl]oxy}pyridin-2-yl)amino]-1-methylpyridin-2(1H)-one | 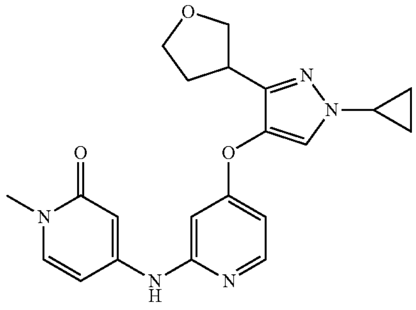 [SMILES: Cn1ccc(Nc2cc(Oc3cn(C4CC4)nc3C3CCOC3)ccn2)cc1=O] | 394 (M + 1) | |
| 42 | N-[4-({l-Cyclopropyl-3-(tetrahydrofuran-3-yl)-1H-pyrazol-4-yl}oxy)pyridin-2-yl]pyridazin-3-amine, isomer 2 | 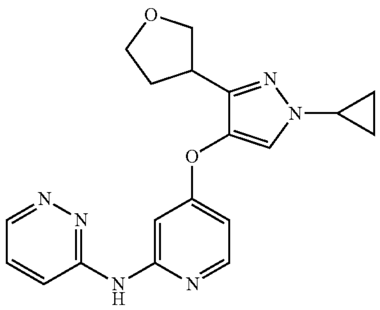 [SMILES: c1cnnc(Nc2cc(Oc3cn(C4CC4)nc3C3CCOC3)ccn2)c1] | 365 (M + 1) | |

TABLE 9-continued

| Ex. No. | Chemical name | Structure | Physical data MS (m/z): | Comments |
|---|---|---|---|---|
| 43 | N-[4-({1-Cyclopropyl-3-(telrahydrofuran-3-yl)-1H-pyrazol-4-yl}oxy)pyridin-2-yl]pyridazin-3-amine, isomer 1 | 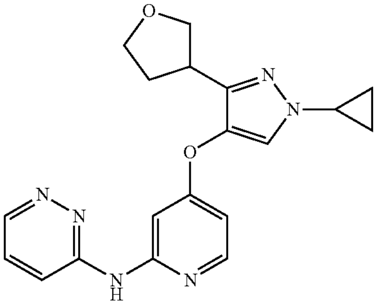 [SMILES: c1cnnc(Nc2cc(Oc3cn(C4CC4)nc3C3CCOC3)ccn2)c1] | 365 (M + 1) | |
| 44 | 2-{5-[(4-{[1-Cyclopropyl-3-(tetrahydrofuran-3-yl)-1H-pyrazol-4-yl]oxy}pyridin-2-yl)amino]pyridin-2-yl}propan-2-ol | 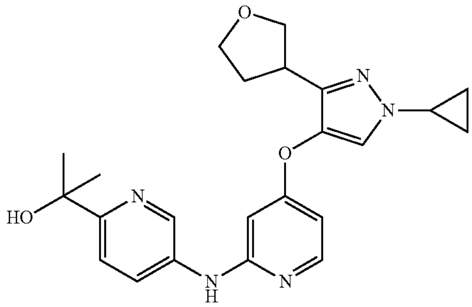 [SMILES: CC(C)(O)c1ccc(Nc2cc(Oc3cn(C4CC4)nc3C3CCOC3)ccn2)cn1] | 422 (M + 1) | sodium phenate, bis(dibenzylidene-acetone)palladium |
| 45 | 2-{5-[(4-{[3-Cyclobutyl-1-(difluoromethyl)-1H-pyrazol-4-yl]oxy}pyridin-2-yl)amino]pyridin-2-yl}propan-2-ol | 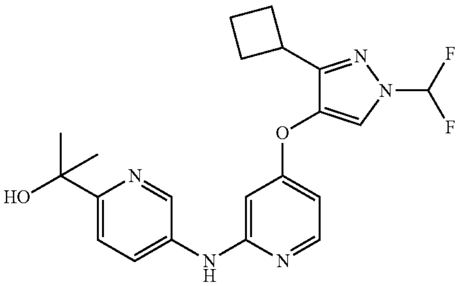 [SMILES: CC(C)(O)c1ccc(Nc2cc(Oc3cn(C(F)F)nc3C3CCC3)ccn2)cn1] | 416 (M + 1) | |
| 46 | 2-[5-({4-[(3-Cyclobutyl-1-cyclopropyl-1H-pyrazol-4-yl)oxy]pyridin-2-yl}amino)pyridin-2-yl]propan-2-ol | 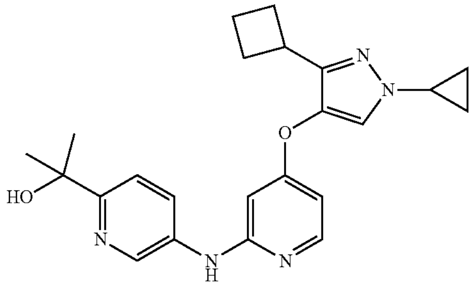 [SMILES: CC(C)(O)c1ccc(Nc2cc(Oc3cn(C4CC4)nc3C3CCC3)ccn2)cn1] | 406 (M + 1) | |
| 47 | 2-{5-[(4-{[1-(Difluoromethyl)-3-(pyridin-2-yl)-1H-pyrazol-4-yl]oxy}pyridin-2-yl)amino]pyridin-2-yl}propan-2-ol | 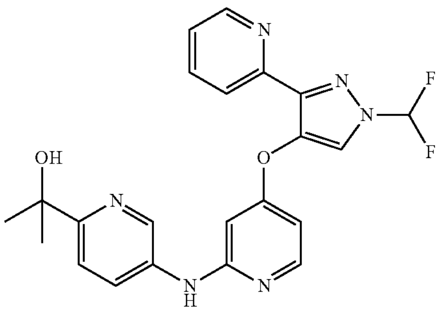 [SMILES: CC(C)(O)c1ccc(Nc2cc(Oc3cn(C(F)F)nc3-c3ccccn3)ccn2)cn1] | 439 (M + 1) | |

TABLE 9-continued

| Ex. No. | Chemical name | Structure | Physical data MS (m/z): | Comments |
|---|---|---|---|---|
| 48 | 2-{4-[(4-{[1-(Difluoromethyl)-3-(pyridin-2-yl)-1H-pyrazol-4-yl]oxy}pyridin-2-yl)amino]pyridin-2-yl}propan-2-ol | 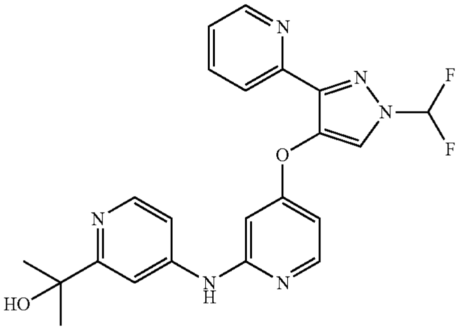 [SMILES: CC(C)(O)c1cc(Nc2cc(Oc3cn(C(F)F)nc3-c3ccccn3)ccn2)ccn1] | 439 (M + 1) | |
| 49 | 2-{5-[(4-{[1-(Propan-2-yl)-3-(pyridin-2-yl)-1H-pyrazol-4-yl]oxy}pyridin-2-yl)amino]pyridin-2-yl}propan-2-ol | 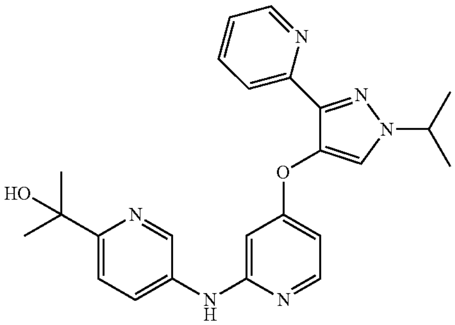 [SMILES: CC(C)n1cc(Oc2ccnc(Nc3ccc(C(C)(C)O)nc3)c2)c(-c2ccccn2)n1] | 431 (M + 1) | |
| 50 | 2-{4-[(4-{[1-(Propan-2-yl)-3-(pyridin-2-yl)-1H-pyrazol-4-yl]oxy}pyridin-2-yl)amino]pyridin-2-yl}propan-2-ol | 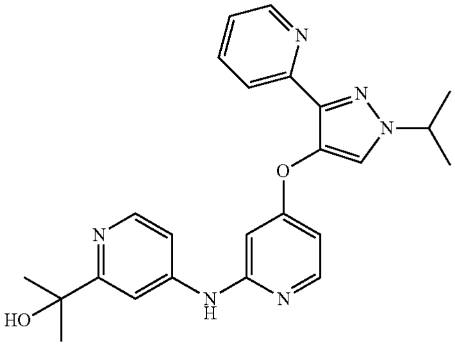 [SMILES: CC(C)n1cc(Oc2ccnc(Nc3ccnc(C(C)(C)O)c3)c2)c(-c2ccccn2)n1] | 431 (M + 1) | |
| 51 | 2-{5-[(4-{[3-Cyclopropyl-1-(difluoromethyl)-1H-pyrazol-4-yl]oxy}pyridin-2-yl)amino]pyridin-2-yl}propan-2-ol | 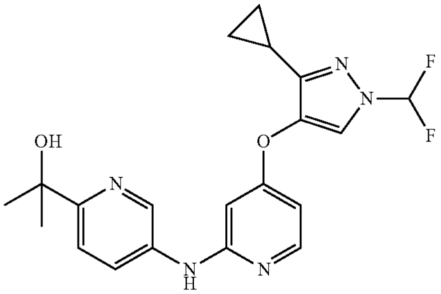 [SMILES: CC(C)(O)c1ccc(Nc2cc(Oc3cn(C(F)F)nc3C3CC3)ccn2)cn1] | 402 (M + 1) | |

TABLE 9-continued

| Ex. No. | Chemical name | Structure | Physical data MS (m/z): | Comments |
|---|---|---|---|---|
| 52 | 2-{4-[(4-{[3-Cyclopropyl-1-(difluoromethyl)-1H-pyrazol-4-yl]oxy}pyridin-2-yl)amino]pyridin-2-yl}propan-2-ol | 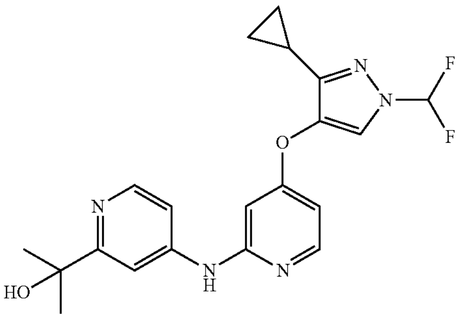 [SMILES: CC(C)(O)c1cc(Nc2cc(Oc3cn(C(F)F)nc3C3CC3)ccn2)ccn1] | 402 (M + 1) | |
| 53 | 2-[5-({4-[(1,3-Dicyclopropyl-1H-pyrazol-4-yl)oxy]pyridin-2-yl}amino)pyridin-2-yl]propan-2-ol | 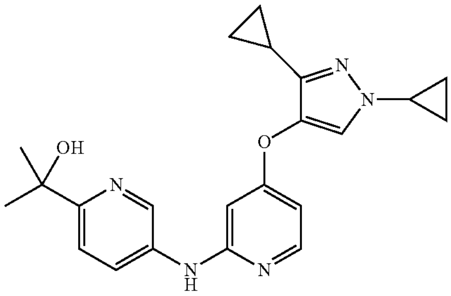 [SMILES: CC(C)(O)c1ccc(Nc2cc(Oc3cn(C4CC4)nc3C3CC3)ccn2)cn1] | 392 (M + 1) | |
| 54 | 2-[4-({4-[(1,3-Dicyclopropyl-1H-pyrazol-4-yl)oxy]pyridin-2-yl}amino)pyridin-2-yl]propan-2-ol | 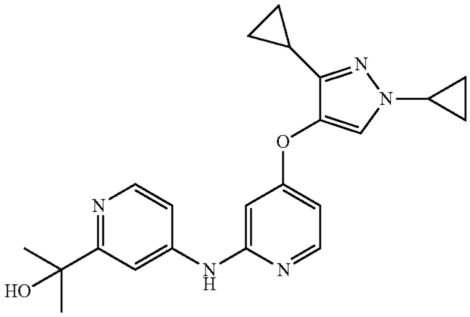 [SMILES: CC(C)(O)c1cc(Nc2cc(Oc3cn(C4CC4)nc3C3CC3)ccn2)ccn1] | 392 (M + 1) | sodium phenate, bis(dibenzylidene-acetone)palladium |
| 55 | 2-{5-[(4-{[3-Cyclopropyl-1-(propan-2-yl)-1H-pyrazol-4-yl]oxy}pyridin-2-yl)amino]pyridin-2-yl}propan-2-ol | 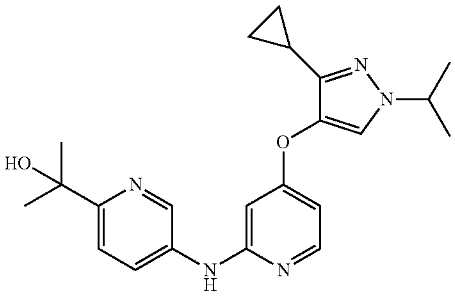 [SMILES: CC(C)n1cc(Oc2ccnc(Nc3ccc(C(C)(C)O)nc3)c2)c(C2CC2)n1] | 394 (M + 1) | sodium phenate, bis(dibenzylidene-acetone)palladium |
| 56 | 2-{5-[(4-{[1-(Difluoromethyl)-3-(tetrahydro-2H-pyran-4-yl)-1H-pyrazol-4-yl]oxy}pyridin-2-yl)amino]pyridin-2-yl}propan-2-ol | 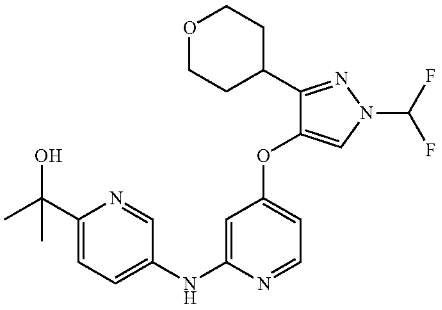 [SMILES: CC(C)(O)c1ccc(Nc2cc(Oc3cn(C(F)F)nc3C3CCOCC3)ccn2)cn1] | 446 (M + 1) | |

TABLE 9-continued

| Ex. No. | Chemical name | Structure | Physical data MS (m/z): | Comments |
|---|---|---|---|---|
| 57 | 2-{4-[(4-{[1-(Difluoromethyl)-3-(tetrahydro-2H-pyran-4-yl)-1H-pyrazol-4-yl]oxy}pyridin-2-yl)amino]pyridin-2-yl}propan-2-ol | 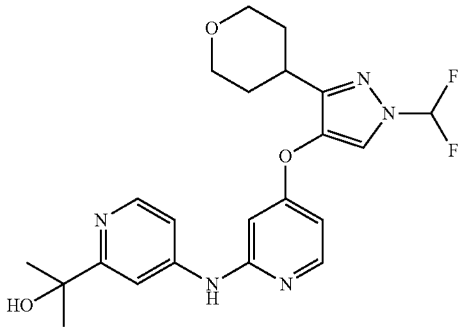 [SMILES: CC(C)(O)c1cc(Nc2cc(Oc3cn(C(F)F)nc3C3CCOCC3)ccn2)ccn1] | 446 (M + 1) | |
| 58 | 2-{5-[(4-{[1-Cyclopropyl-3-(tetrahydro-2H-pyran-4-yl)-1H-pyrazol-4-yl]oxy[pyridin-2-yl)amino]pyridin-2-yl}propan-2-ol | 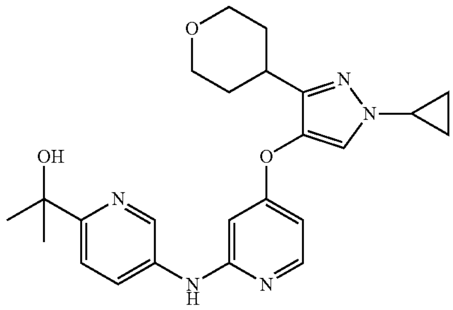 [SMILES: CC(C)(O)c1ccc(Nc2cc(Oc3cn(C4CC4)nc3C3CCOCC3)ccn2)cn1] | 436 (M + 1) | |
| 59 | 2-{4-[(4-{[1-(Propan-2-yl)-3-(tetrahydro-2H-pyran-4-yl)-1H-pyrazol-4-yl]oxy}pyridin-2-yl)amino]pyridin-2-yl}propan-2-ol | 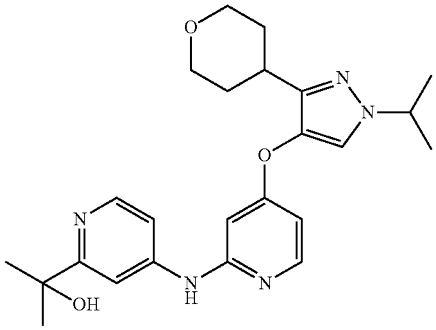 [SMILES: CC(C)n1cc(Oc2ccnc(Nc3ccnc(C(C)(C)O)c3)c2)c(C2CCOCC2)n1] | 438 (M + 1) | |
| 60 | 2-[4-({4-[(3-Cyclobulyl-1-cyclopropyl-1H-pyrazol-4-yl)oxy]pyridin-2-yl}amino)pyridin-2-yl]propan-2-ol | 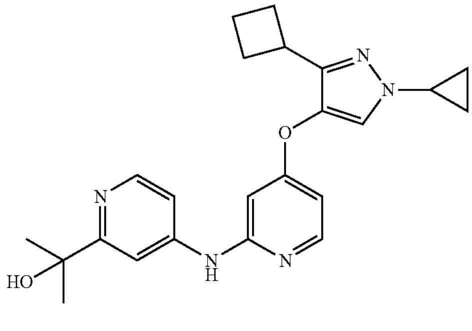 [SMILES: CC(C)(O)c1cc(Nc2cc(Oc3cn(C4CC4)nc3C3CCC3)ccn2)ccn1] | 406 (M + 1) | bis(dibenzylidene-acetone)palladium |

TABLE 9-continued

| Ex. No. | Chemical name | Structure | Physical data MS (m/z): | Comments |
|---|---|---|---|---|
| 61 | 2-{4-[(4-{[3-Cyclobulyl-1-(propan-2-yl)-1H-pyrazol-4-yl]oxy}pyridin-2-yl)amino]pyridin-2-yl}propan-2-ol | 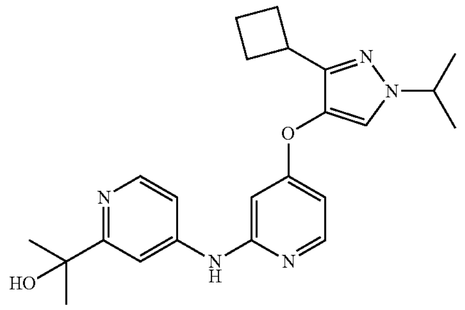 [SMILES: CC(C)n1cc(Oc2ccnc(Nc3ccnc(C(C)(C)O)c3)c2)c(C2CCC2)n1] | 408 (M + 1) | |

EXAMPLE 62

4-[(4-{[1-Cyclopropyl-3-(tetrahydro-2H-pyran-4-yl)-1H-pyrazol-4-yl]oxy}pyridin-2-yl)amino]benzamide

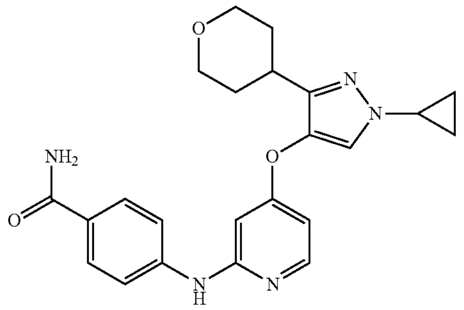 [SMILES: NC(=O)c1ccc(Nc2cc(Oc3cn(C4CC4)nc3C3CCOCC3)ccn2)cc1]

Add potassium carbonate (80.4 mg, 0.58 mmol) to a solution of 4-[[4-(1-cyclopropyl-3-tetrahydropyran-4-yl-pyrazol-4-yl)oxy-2-pyridyl]amino]benzonitrile (467 mg, 1.16 mmol) in DMSO (5 mL). Add 30% hydrogen peroxide (1.77 mL, 17.45 mmol) and stir the reaction mixture at ambient temperature overnight. Dilute with water and extract with DCM four times. Combine the organic layers and wash with saturated aqueous sodium chloride. Dry over anhydrous sodium sulfate. Filter the mixture and concentrate the filtrate under reduced pressure. Purify the residue by reverse phase chromatography (Redisep Rf Gold High Performance C18 Reverse Phase Column, 0-100% formic acid/ACN in formic acid/water) to give the title compound (220 mg; 45.9% yield). MS (m/z): 420 (M+1).

Prepare the following compounds essentially by the method of Example 62.

TABLE 10

| Ex. No. | Chemical name | Structure | Physical data MS (m/z): |
|---|---|---|---|
| 63 | 3-[(4-{[1-Cyclopropyl-3-(tetrahydro-2H-pyran-4-yl)-1H-pyrazol-4-yl]oxy}pyridin-2-yl)amino]benzamide | 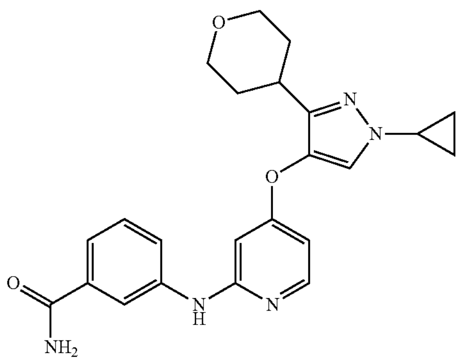 [SMILES: NC(=O)c1cccc(Nc2cc(Oc3cn(C4CC4)nc3C3CCOCC3)ccn2)c1] | 420 (M + 1) |

TABLE 10-continued

| Ex. No. | Chemical name | Structure | Physical data MS (m/z): |
|---|---|---|---|
| 64 | 3-[(4-{[1-(Propan-2-yl)-3-(pyridin-2-yl)-1H-pyrazol-4-yl]oxy}pyridin-2-yl)amino]benzamide | 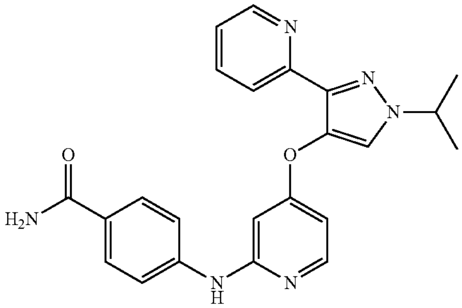 [SMILES: CC(C)n1cc(Oc2ccnc(Nc3ccc(C(N)=O)cc3)c2)c(-c2ccccn2)n1] | 415 (M + 1) |
| 65 | 4-({4-[(1-Cyclopropyl-3-ethyl-1H-pyrazol-4-yl)oxy]pyridin-2-yl}amino)benzamide | 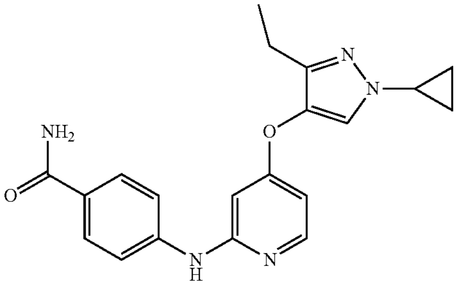 [SMILES: CCc1nn(C2CC2)cc1Oc1ccnc(Nc2ccc(C(N)=O)cc2)c1] | 364 (M + 1) |
| 66 | 4-[(4-{[1-(Difluoromethyl) 3-(tetrahydro-2H-pyran-4-yl)-1H-pyrazol-4-yl]oxy}pyridin-2-yl)amino]benzamide | 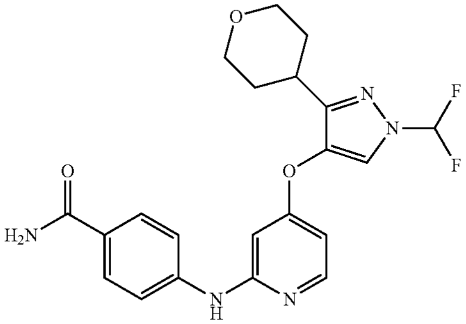 [SMILES: NC(=O)c1ccc(Nc2cc(Oc3cn(C(F)F)nc3C3CCOCC3)ccn2)cc1] | 430 (M + 1) |
| 67 | 4-[(4-{[3-Cyclobutyl-1-(difluoromethyl)-1H-pyrazol-4-yl]oxy}pyridin-2-yl)amino]benzamide | 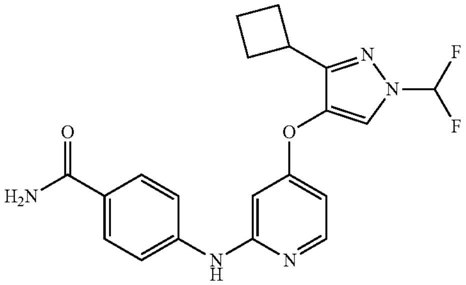 [SMILES: NC(=O)c1ccc(Nc2cc(Oc3cn(C(F)F)nc3C3CCC3)ccn2)cc1] | 400 (M + 1) |
| 68 | 3-[(4-{[1-(Difluoromethyl)-3-(pyridin-2-yl)-1H-pyrazol-4-yl]oxy}pyridin-2-yl)amino]benzamide | 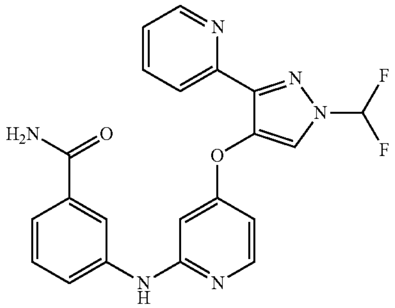 [SMILES: NC(=O)c1cccc(Nc2cc(Oc3cn(C(F)F)nc3-c3ccccn3)ccn2)c1] | 423 (M + 1) |

TABLE 10-continued

| Ex. No. | Chemical name | Structure | Physical data MS (m/z): |
|---|---|---|---|
| 69 | 4-({4-[(1,3-Dicyclopropyl-1H-pyrazol-4-yl)oxylpyridin-2-yl}amino)benzamide | 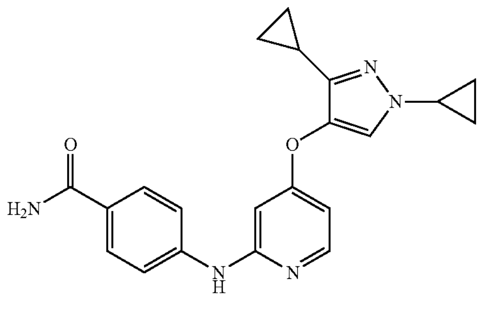 [SMILES: NC(=O)c1ccc(Nc2cc(Oc3cn(C4CC4)nc3C3CC3)ccn2)cc1] | 376 (M + 1) |

EXAMPLE 70

2-{4-[(4-{[3-Cyclopropyl-1-(propan-2-yl)-1H-pyrazol-4-yl]oxy}pyridin-2-yl)amino]pyridin-2-yl}propan-2-ol

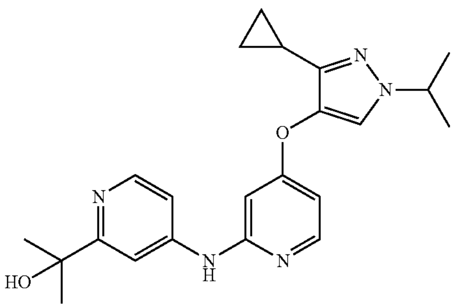 [SMILES: CC(C)n1cc(Oc2ccnc(Nc3ccnc(C(C)(C)O)c3)c2)c(C2CC2)n1]

Purge a solution of methyl 4-[[4-(3-cyclopropyl-1-isopropyl-pyrazol-4-yl)oxy-2-pyridyl]amino]pyridine-2-carboxylate (298 mg, 0.76 mmol) in THF (6 mL) in a sealed vial with nitrogen. Add methylmagnesium bromide (3M in diethyl ether, 1.01 mL, 3.03 mmol) dropwise and stir the mixture at room temperature for two hours. Concentrate the mixture under reduced pressure and dilute the residue with DCM and saturated aqueous sodium bicarbonate. Isolate the organic layer and extract the aqueous layer with DCM. Combine the organic layers and wash with saturated aqueous sodium chloride. Dry over sodium sulfate, filter and concentrate the filtrate. Purify by silica gel column chromatography with 5-10% MeOH in DCM to give the title compound (160 mg; 53.69% yield). MS (m/z): 394 (M+1).

EXAMPLE 71

2-{5-[(4-{[3-(Pyridin-2-yl)-1H-pyrazol-4-yl]oxy}pyridin-2-yl)amino]pyridin-2-yl}propan-2-ol

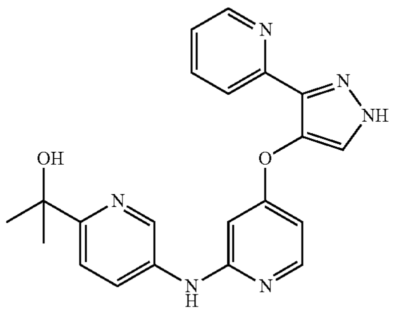 [SMILES: CC(C)(O)c1ccc(Nc2cc(Oc3c[nH]nc3-c3ccccn3)ccn2)cn1]

Cool a solution of 2-[5-[[4-[3-(2-Pyridyl)-1-(2-trimethylsilylethoxy-methyl)pyrazol-4-yl]oxy-2-pyridyl]amino]-2-pyridyl]propan-2-ol (500 mg, 0.96 mmol) in trifluoroacetic acid (3 mL) to 0° C. in an ice bath. Add triethylsilane (1 mL, 6.24 mmol). Stir the reaction mixture at room temperature overnight. Concentrate and purify the residue by reverse phase chromatography (Redisep Rf Gold High Performance C18 Reverse Phase Column, 0-100% 10 mM ammonium bicarbonate in ACN). Concentrate the appropriate fractions to remove ACN. Extract the remaining aqueous mixture with DCM, isolate organic layer, and dry over sodium sulfate. Filter and concentrate the filtrate under reduced pressure to give the title compound (168 mg; 44.9% yield). MS (m/z): 389 (M+1).

EXAMPLE 72

N-[4-({1-(Difluoromethyl)-3-(tetrahydrofuran-3-yl)-1H-pyrazol-4-yl}oxy)pyridin-2-yl]pyridazin-3-amine, isomer 1

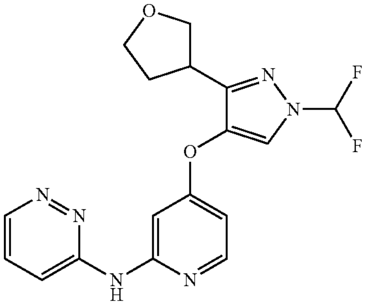 [SMILES: FC(F)n1cc(Oc2ccnc(Nc3cccnn3)c2)c(C2CCOC2)n1]

Purify the racemic mixture of N-[4-[1-(difluoromethyl)-3-tetrahydrofuran-3-yl-pyrazol-4-yl]oxy-2-pyridyl] pyridazin-3-amine (Preparation 49) with chiral chromatography to afford the first eluting enantiomer as the title compound. MS (m/z): 375 (M+1).

Purification conditions: CHIRALPAK® IC; Mobile Phase: 30% isopropanol containing 0.2% isopropyl amine in carbon dioxide; Flow rate: 70 g/minute; UVW: 280 nm; Retention time: 3.93 minutes.

Prepare the following compound essentially by the method of Example 72. Alternate purification conditions are indicated.

TABLE 11

| Ex. No. | Chemical name | Structure | conditions | Physical data |
|---|---|---|---|---|
| 73 | 2-(5-{[4-({1-Cyclopropyl-3-(tetrahydrofuran-3-yl)-1H-pyrazol-4-yl}oxy)pyridin-2-yl]amino}pyridin-2-yl)propan-2-ol, isomer 1 | 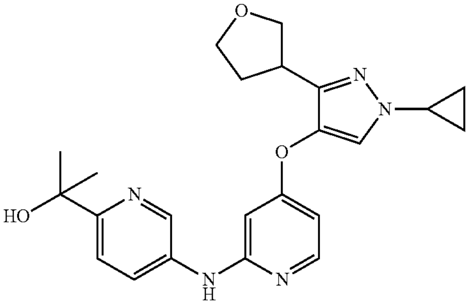 [SMILES: CC(C)(O)c1ccc(Nc2cc(Oc3cn(C4CC4)nc3C3CCOC3)ccn2)cn1] | CHIRALCEL ® OJ-H; Mobile Phase: 20% EtOH in heptane; Flow rate: 425 mL/minutes; UVW: 280 nm; Retention Time: 17.39 minutes | MS (m/z): 422 (M + 1) |
| 74 | 2-(5-{[4-({1-Cyclopropyl-3-(tetrahydrofuran-3-yl)-1H-pyrazol-4-yl}oxy)pyridin-2-yl]amino}pyridin-2-yl)propan-2-ol, isomer 2 | 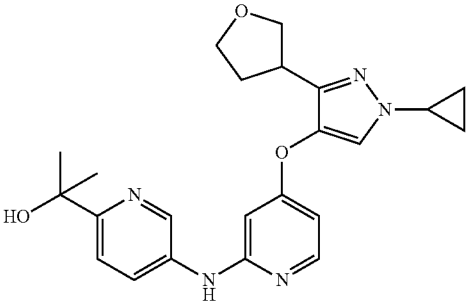 [SMILES: CC(C)(O)c1ccc(Nc2cc(Oc3cn(C4CC4)nc3C3CCOC3)ccn2)cn1] | CHIRALCEL ® OJ-H; Mobile Phase: 20% EtOH in heptane; Flow rate: 425 mL/minutes; UVW: 280 nm; Retention Time: 21.55 minutes | MS (m/z): 422 (M + 1) |
| 75 | 2-(4-{[4-({1-Cyclopropyl-3-(tetrahydrofuran-3-yl)-1H-pyrazol-4-yl}oxy)pyridin-2-yl]amino}pyridin-2-yl)propan-2-ol, isomer 1 | 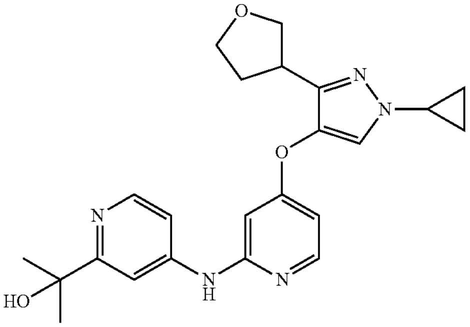 [SMILES: CC(C)(O)c1cc(Nc2cc(Oc3cn(C4CC4)nc3C3CCOC3)ccn2)ccn1] | CHIRALCEL ® OJ-H; Mobile Phase: 20% isopropanol containing 0.2% isopropyl amine in carbon dioxide; Flow rate: 70 g/minute; UVW: 225 nm; Retention Time: 2.67 minutes | MS (m/z): 422 (M + 1) |

TABLE 11-continued

| Ex. No. | Chemical name | Structure | conditions | Physical data |
|---|---|---|---|---|
| 76 | 2-(4-{[4-({1-Cyclopropyl-3-(tetrahydrofuran-3-yl)-1H-pyrazol-4-yl}oxy)pyridin-2-yl]amino}pyridin-2-yl)propan-2-ol, isomer 2 | 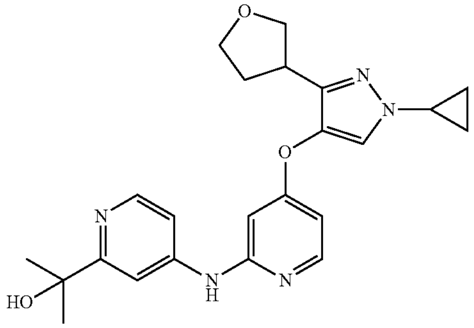 [SMILES: CC(C)(O)c1cc(Nc2cc(Oc3cn(C4CC4)nc3C3CCOC3)ccn2)ccn1] | CHIRALCEL ® OJ-H; Mobile Phase: 20% isopropanol containing 0.2% isopropyl amine in carbon dioxide; Flow rate: 70 g/minute; UVW: 225 nm; Retention Time: 3.59 minutes | MS (m/z): 422 (M + 1) |

X-Ray Powder Diffraction Collection Procedure for Examples 77-79

Obtain the XRD patterns of crystalline solids on a Bruker D4 Endeavor X-ray powder diffractometer, equipped with a CuKa source ($\lambda$=1.54060 Å) and a Vantec detector, operating at 35 kV and 50 mA. Scan the sample between 4 and 40° in 2θ, with a step size of 0.009° in 2θ and a scan rate of 0.5 seconds/step, and with 0.6 mm divergence, 5.28 fixed anti-scatter, and 9.5 mm detector slits. Pack the dry powder on a quartz sample holder and obtain a smooth surface using a glass slide. Collect the crystal form diffraction patterns at ambient temperature and relative humidity.

EXAMPLE 77

2-{4-[(4-{[1-Cyclopropyl-3-(tetrahydro-2H-pyran-4-yl)-1H-pyrazol-4-yl]oxy}pyridin-2-yl)amino]pyridin-2-yl}propan-2-ol, (2Z)-but-2-enedioate (1:1)

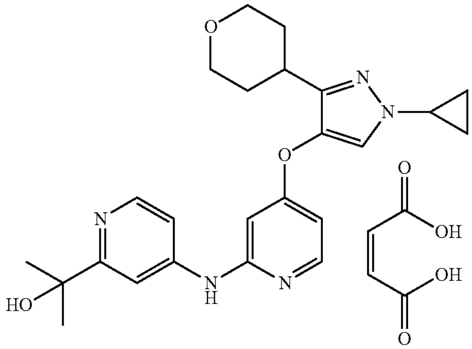

Add 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol (142 mg) in ACN (2 mL). The solid dissolves completely while stirring at 80° C./1000 rpm. Add maleic acid (48 mg, 1.20 equivalents, in 1 mL of ACN at 80° C.) to the resulting solution. The mixture is cloudy initially but quickly becomes a clear solution. Stop heating and stirring. Cool the solution to room temperature. Add another 2 mL of ACN to suspend the solid. Isolate the white solid by vacuum filtration and dry the solid in place on the filter for 15 minutes under an air stream. Dry the resulting solid in a 65° C. vacuum oven overnight to afford the title compound (132 mg, 73.4% yield). The theoretical percentage of maleic acid ion in the formed salt for a mono salt is 21.0%. Counterion analysis by HPLC determines that the actual percentage of maleic acid ion in the formed salt is 17.2%. The counterion analysis indicates a mono salt.

X-Ray Powder Diffraction of Example 77

A prepared sample of Example 77 is characterized by an XRD pattern using CuKa radiation as having diffraction peaks (2-theta values) as described in Table 13 below, and in particular having peaks at 9.6° in combination with one or more of the peaks selected from the group consisting of 12.5°, 17.5°, and 16.9°; with a tolerance for the diffraction angles of 0.2 degrees.

TABLE 12

X-ray powder diffraction peaks of Example 77

| Peak | Angle (°2-Theta) +/− 0.2° | Relative Intensity (% of most intense peak) |
|---|---|---|
| 1 | 9.6 | 100.0 |
| 2 | 12.5 | 88.2 |
| 3 | 17.5 | 74.4 |
| 4 | 16.9 | 55.8 |
| 5 | 12.9 | 54.0 |
| 6 | 20.1 | 45.9 |
| 7 | 21.5 | 44.1 |
| 8 | 19.2 | 36.4 |
| 9 | 20.9 | 35.5 |
| 10 | 23.5 | 32.0 |

EXAMPLE 78

2-{4-[(4-{[1-Cyclopropyl-3-(tetrahydro-2H-pyran-4-yl)-1H-pyrazol-4-yl]oxy}pyridin-2-yl)amino]pyridin-2-yl}propan-2-ol, methanesulfonate (1:1)

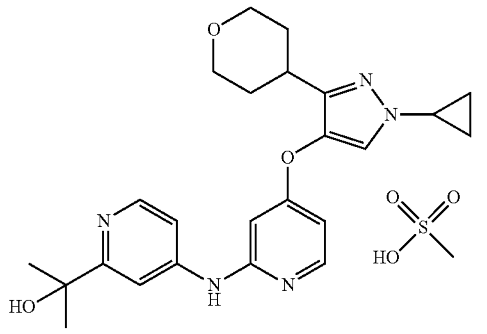

Add 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol (113 mg) in acetone (2 mL). The solid dissolves completely while stirring at 60° C./1000 rpm. Add methanesulfonic acid (21 μL, 1.24 equivalents) to the resulting solution. Stop heating and stirring. Cool the solution to room temperature. Add another 3 mL of acetone to suspend the solid. Isolate the white solid by vacuum filtration and dry the solid in place on the filter for 15 minutes under air stream. Dry the resulting solid in a 65° C. vacuum oven overnight to afford the title compound (87 mg, 63.08% yield). The theoretical percentage of methanesulfonic acid ion in the formed salt for a mono salt is 18.1%. Counterion analysis by HPLC determines that the actual percentage of methanesulfonic acid ion in the formed salt is 16.2%. The counterion analysis indicates a mono salt.

X-Ray Powder Diffraction of Example 78

A prepared sample of Example 78 is characterized by an XRD pattern using CuKa radiation as having diffraction peaks (2-theta values) as described in Table 14 below, and in particular having peaks at 7.0° in combination with one or more of the peaks selected from the group consisting of 14.1°, 10.8°, and 18.6°; with a tolerance for the diffraction angles of 0.2 degrees.

TABLE 13

X-ray powder diffraction peaks of Example 78

| Peak | Angle (°2-Theta) +/− 0.2° | Relative Intensity (% of most intense peak) |
|---|---|---|
| 1 | 7.0 | 100.0 |
| 2 | 14.1 | 93.2 |
| 3 | 10.8 | 73.6 |
| 4 | 18.6 | 66.1 |
| 5 | 15.9 | 61.4 |
| 6 | 19.7 | 60.7 |
| 7 | 5.4 | 49.2 |
| 8 | 7.9 | 49.1 |
| 9 | 4.5 | 48.1 |
| 10 | 17.8 | 47.6 |

EXAMPLE 79

2-{4-[(4-{[1-Cyclopropyl-3-(tetrahydro-2H-pyran-4-yl)-1H-pyrazol-4-yl]oxy}pyridin-2-yl)amino]pyridin-2-yl}propan-2-ol 4-methylbenzenesulfonate (1:1)

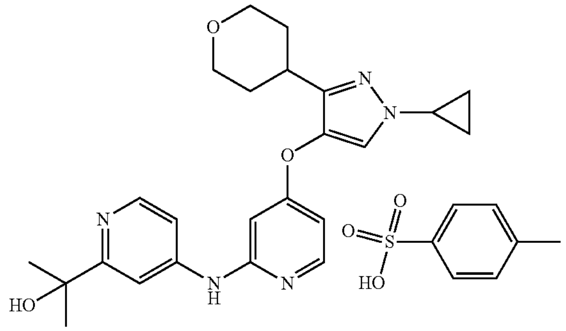

Add 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol (122 mg) in EtOAc (2 mL). Dissolve the solid completely while stirring at 80° C./1000 rpm. Add p-toluenesulfonic acid monohydrate (1.23 equivalents, in 1 mL of EtOAc at 80° C.) to the resulting solution. Slurry the mixture at 80° C./1000 rpm for 30 minutes. Turn off the heat and keep stirring the mixture at 1000 rpm as it cools to room temperature. Isolate the resulting white solid by vacuum filtration and dry the solid in place on the filter for 15 minutes under air stream. Dry the resulting solid in a 65° C. vacuum oven overnight to afford the title compound (159 mg, 93.40% yield). The theoretical percentage of p-toluenesulfonic acid ion in the formed salt for a mono salt is 29.3%. Counterion analysis by HPLC determines that the actual percentage of p-toluenesulfonic acid ion in the formed salt is 28.3%. The counterion analysis indicates a mono salt.

X-Ray Powder Diffraction of Example 79

A prepared sample of Example 79 is characterized by an XRD pattern using CuKa radiation as having diffraction peaks (2-theta values) as described in Table 15 below, and in particular having peaks at 17.8° in combination with one or more of the peaks selected from the group consisting of 19.7°, 18.4°, and 22.0°; with a tolerance for the diffraction angles of 0.2 degrees.

TABLE 14

X-ray powder diffraction peaks of Example 79

| Peak | Angle (°2-Theta) +/− 0.2° | Relative Intensity (% of most intense peak) |
|---|---|---|
| 1 | 17.8 | 100.0 |
| 2 | 19.7 | 78.0 |
| 3 | 18.4 | 65.8 |
| 4 | 22.0 | 53.0 |
| 5 | 20.3 | 50.5 |
| 6 | 10.1 | 48.0 |
| 7 | 16.4 | 46.5 |
| 8 | 11.5 | 24.6 |
| 9 | 7.4 | 14.2 |
| 10 | 7.8 | 13.1 |

Signaling via the TGFβ pathway has been associated with cancer and tumor progression in several indications (Elliott et. al. (2005) J Clin Oncol 23:2078; Levy et. al. (2006) Cytokine & Growth Factor Rev 17:41-58). There are several types of cancer where TGFβ ligands produced by the tumor or by the stroma in the tumor microenvironment may participate in tumor progression. MATLyLu rat prostate cancer cells (Steiner and Barrack (1992) Mol. Endocrinol 6:15-25) and MCF-7 human breast cancer cells (Arteaga, et al. (1993) Cell Growth and Differ. 4:193-201) became more tumorigenic and metastatic after transfection with a vector expressing the mouse TGFβ1. TGF-β1 has been associated with angiogenesis, metastasis and poor prognosis in human prostate and advanced gastric cancer (Wikstrom, P., et al. (1998) Prostate 37: 19-29; Saito, H. et al. (1999) Cancer 86: 1455-1462). In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGFβ1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGFβ1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGFβ1 have been shown to indicate poor prognosis for advanced breast cancer patients (Anscher, et al. (1993) N. Engl. J. Med. 328:1592-1598). Patients with high circulating TGFβ before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGFβ can be used to identify at risk patients and 2) that reduction of TGFβ signaling could decrease the morbidity and mortality of these common treatments for breast cancer patients.

Recent publications have also suggested that TGFβ signaling may be important in driving resistance of tumors to standard of care therapies, including chemotherapies and receptor tyrosine kinases (WO2012138783). Specifically, in colon cancer, a specific gene expression signature has been shown to isolate a group of patients who are resistant to common first line treatments. These tumor cells regain sensitivity to therapy when the TGFβ pathway is blocked with a TGFβRI specific small molecule inhibitor (Huang, et. al. (2012) Cell 151:937-950; Sadanandam et. al. (2013) Nat Med 19:619-625; Vermeulen et. al. (2013) Nat Ned 19:614-618; Roepman et. al. (2014) 134:552-562).

Myleodysplastic syndromes (MDS) are disorders of the hematopoietic system in the myeloid compartment and are characterized by ineffective production of myeloid cells. MDS is linked to alterations of the TGFβ pathway represented by reduced SMAD7 levels. SMAD7 is an inhibitory SMAD which functions to inhibit TGFβ mediated SMAD signaling and is downstream of ligand activated signaling through TGFβRI and TGFβRII. Overexpression of SMAD7 is thus thought to lead to over-activation of TGFβ signaling in MDS, and this phenotype can be reversed by treating with a TGFβRI small molecule inhibitor (Zhou et. al. (2011) Cancer Res. 71:955-963). Similarly, in glioblastoma (GBM), TGFβ ligand levels are elevated and related to disease progression. An antisense oligonucleotide therapeutic, AP1002, has been shown to be potentially active in a subset of GBM patients (Bogdahn et. al. (2011). Curr Pharm Biotechnol). In melanoma, TGFβ pathway signaling activation has also been linked to resistance to BRAF and MEK inhibitors (Sun et. al. (2014) Nature. 508:118-122).

Many malignant cells secrete transforming growth factor-β (TGF-β), a potent immunosuppressant, suggesting that TGFβ production may represent a significant tumor escape mechanism from host immunosurveillance (Flavell et. al. (2010) Nat Rev Immunol 10:554-567; Kast et. al. (1999) Leukemia 13:1188-1199). Establishment of a leukocyte subpopulation with disrupted TGFβ signaling in the tumor-bearing host offers a potential means for immunotherapy of cancer alone or in combination with one or more other immunotherapies, for example in combination with one or more PD-1 inhibitor such as nivolumab, pembrolizumab, PD-L1 inhibitors, cancer vaccines, and bispecific immune engaging molecules such as IMCgp100. TGFβ ligand produced by lymphocytes has been shown preclinically to antagonize tumor immune surveillance (Donkor et. al. (2012) Development. Oncoimmunology 1:162-171, Donkor et. al. (2011) Cytokine Immunity 35:123-134); disrupting this axis preclinically has been shown to provide anti-tumor benefit in murine models and in vitro (Zhong et. al. (2010) Cancer Res 16:1191-1205; Petrausch et. al. (2009) J Immunol 183:3682-3689); Wakefield et. al. (2013) Nat. Rev Cancer 13:328-341). A transgenic animal model with disrupted TGFβ signaling in T cells is capable of eradicating a normally lethal TGFβ over expressing lymphoma tumor, EL4 (Gorelik and Flavell, (2001) Nature Medicine 7(10): 1118-1122). Down regulation of TGFβ secretion in tumor cells results in restoration of immunogenicity in the host, while T-cell insensitivity to TGFβ results in accelerated differentiation and autoimmunity, elements of which may be required in order to combat self-antigen-expressing tumors in a tolerized host. The immunosuppressive effects of TGFβ have also been implicated in a subpopulation of HIV patients with lower than predicted immune response based on their CD4/CD8 T cell counts (Garba, et al. J. Immunology (2002) 168: 2247-2254). A TGFβ neutralizing antibody was capable of reversing the effect in culture, indicating that TGFβ signaling inhibitors may have utility in reversing the immune suppression present in this subset of HIV patients.

During the earliest stages of carcinogenesis, TGFβ1 can act as a potent tumor suppressor and may mediate the actions of some chemopreventive agents. However, at some point during the development and progression of malignant neoplasms, tumor cells appear to escape from TGFβ-dependent growth inhibition in parallel with the appearance of bioactive TGFβ in the microenvironment. The dual tumor suppression/tumor promotion roles of TGFβ have been most clearly elucidated in a transgenic system over expressing TGFβ in keratinocytes. While the transgenics were more resistant to formation of benign skin lesions, the rate of metastatic conversion in the transgenics was dramatically increased (Cui, et al (1996) Cell 86(4):531-42). The production of TGFβ1 by malignant cells in primary tumors appears to increase with advancing stages of tumor progression. Studies in many of the major epithelial cancers suggest that the increased production of TGFβ by human cancers occurs as a relatively late event during tumor progression. Further, this tumor-associated TGFβ provides the tumor cells with a selective advantage and promotes tumor progression. The effects of TGFβ on cell/cell and cell/stroma interactions result in a greater propensity for invasion and metastasis. Tumor-associated TGFβ may allow tumor cells to escape from immune surveillance since it is a potent inhibitor of the clonal expansion of activated lymphocytes. TGFβ has also been shown to inhibit the production of angiostatin. Cancer therapeutic modalities such as radiation therapy and chemotherapy induce the production of activated TGFβ in the tumor, thereby selecting outgrowth of malignant cells that are resistant to TGFβ growth inhibitory effects. Thus, these anticancer treatments increase the risk and hasten the development of tumors with enhanced growth and invasiveness. In this situation, agents targeting TGFβ-mediated signal transduction might be a very effective therapeutic strategy. The resistance of tumor cells to TGFβ has been shown to negate much of the cytotoxic effects of radiation therapy and chemotherapy and the treatment-dependent activation of TGFβ in the stroma may even be detrimental as it can make the microenvironment more conducive to tumor progression and contributes to tissue damage leading to fibrosis. The development of TGFβ signal transduction inhibitors is likely to benefit the treatment of progressed cancer alone and in combination with other therapies.

Additionally, it is known in the art that TGFβ signaling is involved in fibrotic conditions such as liver fibrosis and chronic kidney disease. See for example, Ueha S, et. al. 2012. *Front Immunol.* 3:71. Cellular and molecular mechanisms of chronic inflammation-associated organ fibrosis; Bottinger et al. 2002. *J Amer Soc Nephrol.* 13:2600. TGF-β Signaling in Renal Disease; Trachtman H., et al. 2011. Kidney International 79:1236. A phase 1, single-dose study of fresolimumab, an anti-TGF-β antibody, in treatment-resistant primary focal segmental glomerulosclerosis; and Rosenbloom J, et. al. 2010. Narrative review: fibrotic diseases: cellular and molecular mechanisms and novel therapies. *Ann Intern Med* 152: 159-166.

The following assays demonstrate that the exemplified compounds inhibit TGFβR1 in a biochemical assay, at the cellular level, and in an animal model.

Biochemical Assay for TGFβR1 Activity

The purpose of this in vitro assay is to identify compounds that inhibit TGFβR1.

Protein Expression and Purification

Insert the nucleotide sequence encoding amino acids 200-503 of human TGFβR1 (NM_004612.2) with amino acid Thr at position 204 changed to Asp into PFASTBAC™ 1 (Invitrogen, Cat#10360-014) vector with N-terminal HIS tag. Generate baculovirus according to the protocol of the BAC-TO-BAC® Baculovirus Expression System (Invitrogen, Cat#10359-016). Infect Sf9 cells at $1.5\times10^6$ cells/mL using 15 mL P1 virus per liter of culture and incubate at 28° C. for 48 hours. Harvest the cells and store at −80° C. for subsequent protein purification. Conduct protein purification at 4° C. Suspend pellets from 2 L culture in 100 mL buffer A (50 mM Tris-HCl, pH8, 200 mM NaCl, 1 mM DTT, 5 mM imidazole, 10% glycerol) containing 0.2% Triton X-100 and Roche complete EDTA-free protease inhibitor cocktail and homogenize. Clarify the cell lysates by centrifugation in a Bechman JA-18 rotor for 45 minutes at 16,500 rpm. Incubate the supernatant with 5 mL of Ni-NTA metal affinity resin (Qiagen) for three hours. Pack the resin onto a column and wash with buffer A. Elute the HIS-TGFβR1(200-503)(T204D) protein with 0-400 mM imidazole gradient in buffer A. Pool and concentrate the HIS-TGFβR1(200-503)(T204D) containing fractions and load onto a HiLoad 16.600 Superdex 200 column (GE Healthcare Bioscience). Elute the column with storage buffer (50 mM Tris-HCl, pH7.5, 150 mM NaCl, 1 mM DTT). Pool and concentrate the HIS-TGFβR1(200-503)(T204D) containing fractions. Determine the protein concentration by UV280. Aliquot the protein and store at −80° C.

TR-FRET Assay Conditions

Pre-incubate compounds with recombinant His-TGFβR1 (200-503)(T204D), and Eu-anti-HIS detection antibodies (InVitrogen, Cat# PV5597) in half-area black plates. Prepare compound serial dilutions from 1 mM stock test compounds in DMSO. Serially dilute the stock solution 3-fold in DMSO to obtain a ten-point dilution curve with final compound concentrations ranging from 2 μM to 0.1 nM. The final DMSO concentration in the assay is 4%. Initiate the reaction with the addition of kinase tracer (Kinase Tracer 178, Life Technologies PR9080A, InVitrogen). After 45-60 minutes, read the fluorescence on a plate reader.

Calculate percent inhibition of compound treated groups relative to the minimum inhibition group (DMSO alone, untreated). Calculate absolute $IC_{50}$ using a 4-parameter nonlinear logistic equation where absolute $IC_{50}$=concentration causing 50% inhibition using Activity-Base data analysis software. The results of these assays demonstrate that the exemplified compounds are effective inhibitors of TGFβR1. For example, all exemplified compounds demonstrate $IC_{50}$ values less than 1 μM. Specifically, the $IC_{50}$ for Example 1 is 0.027 μM.

Cell-Based Luciferase Reporter Assay for TGFβR1 Activity

The purpose of this assay is to identify compounds that selectively interfere with SMAD 2,3-dependent gene expression in cell-based assays demonstrating that they inhibit TGFβR1 at the cellular level.

Engineer HEK293 cells (ATCC, CRL-1573) to express firefly luciferase from a SMAD 2,3-responsive promoter in response to TGFβ stimulation. Such a cell line may be generated via infection with lentiviral particles (SA Biosciences) and selection for puromycin resistance. Plate the HEK293_SMAD 2/3 cells from assay-ready frozen stocks at 15,000 cells per well in 96-well plates in OPTI-MEM® medium containing 10% fetal bovine serum. After 72 hours, change the medium to OPTI-MEM® containing 0.1% bovine serum albumin Prepare test compounds in DMSO to make 10 mM stock solutions. Serially dilute the stock solutions 3-fold in DMSO to obtain a ten-point dilution curve with final compound concentrations ranging from 20 μM to 1 nM with the final DMSO concentration in the assay is 0.5%. Add the test compounds and after a one hour equilibration, add TGFβ (final concentration=2 nM, R&D Systems).

After 24 hours, add lysis buffer [Glo Lysis Buffer (Cat #E2661)] and luciferase reagent [Promega Bright Glo Luciferase Reagent (Cat #E2620)] to each well to double the well volume. Transfer aliquots (80 μL) to white solid bottom plates for reading luminescence on a plate reader (Emission filter: Luminescence 700, 1 second read). Calculate percent inhibition of compound treated groups relative to the minimum inhibition group (DMSO alone, untreated). Calculate the relative $IC_{50}$ for each compound from a dose response study and is the concentration necessary to achieve 50% inhibition. Fit the data generated from the dose-response studies to a four-parameter logistic equation using ActivityBase data analysis software. The results of these assays demonstrate that the exemplified compounds are effective inhibitors of luciferase reporter activity from TGFβ-stimulated HEK293_SMAD2/3 cells. For example, all exemplified compounds demonstrate $IC_{50}$ values less than 1 μM. Specifically, the $IC_{50}$ for Example 1 is 0.0824 μM (±0.005, n=2).

IVTI Assay

The purpose of this assay is to measure the ability of a test compound to inhibit the pSMAD2 expression in tumors in an EMT6-LM2 syngeneic animal model, in other words, the assay measures the ability of a test compound to inhibit TGFβR1 signaling in a solid tumor animal model.

EMT6-LM2 Cell Generation

Implant EMT-6 cells (ATCC, CRL-2755) subcutaneously ($5\times10^5$/animal) to the flank of immune competent BALB/cAnNHsd mice (Harlan Laboratories). When tumors reach approximately 3000 $mm^3$, sacrifice the animals by $CO_2$ asphyxiation. Isolate the lungs from tumor bearing animals and place in culture. Gently homogenize the lungs to create a single cell suspension. Grow cells in culture media (IMDM, 10% FBS) and isolate the tumor cells to give EMT6-LM1 cells. Repeat the above process by using EMT6-LM1 cells for implantation to generate EMT-LM2 cells.

Purified Phospho HIS-SMAD2 (pSMAD2)

Insert the nucleotide sequence encoding full-length human SMAD2 (NM_005901.5) into PFASTBACHTA™ (Invitrogen, Cat #10584-027) vector, resulting in the baculovirus construct for expressing HIS-SMAD2 protein. Insert the nucleotide sequence encoding amino acids 148-503 of human TGFβR1 (NM_004612.2) with amino acid Thr at position 204 changed to Asp into PFASTBACHTA™ (Invitrogen, Cat #10584-027) vector, resulting in the baculovirus construct for expressing HIS-TGFβR1(148-503)(T204D) protein. Generate baculovirus according to the protocol of the BAC-TO-BAC® Baculovirus Expression System (Invitrogen). Infect Sf9 cells at $1.5\times10^6$ cells/mL using 10 mL P1 virus of HIS-SMAD2 and P1 virus of HIS-TGFβR1(148-503)(T204D) per liter of culture and incubate at 28° C. for 45 hours. Add okadaic acid to a final concentration of 0.1 μM. After an additional three hours of incubation, harvest the cells and store at −80° C. for subsequent protein purification. Conduct protein purification at 4° C. Lys frozen cell pellets from 6 L culture by incubation with stirring in 300 mL of cold buffer A (50 mM sodium phosphate, pH7.5, 300 mM NaCl, 2 mM β-mercaptoethanol, 5 mM imidazol, 10% glycerol, 0.1 okadaic acid) containing 0.1% TRITON® X-100 and Roche complete EDTA-free protease inhibitor cocktail and homogenization. Clarify cell lysates by centrifugation in a Bechman JA-18 rotor for 45 minutes at 16,500 rpm. Incubate the supernatant with 10 mL of TALON metal affinity resin (Clontech, Cat#635504) for two hours. Wash the batch with 100 mL of buffer A containing 0.1% TRITON® X-100. Pack the resin onto a column and wash with buffer A. Elute the HIS-SMAD2 protein with a 0-100 mM imidazole gradient in buffer A. Pool the fractions containing phospho HIS-SMAD2 and supplement with 0.1 μM okadiac acid and 5 mM EDTA. Determine the protein concentration by the BioRad protein assay (BioRad DC Protein Assay kit #500-0116) using BSA as standard. Aliquot the protein and store at −80° C.

Live Phase

Culture EMT6-LM2 cells in Iscoves Modified Dulbecco's Media (MDM) supplemented with 10% FBS, 2 mM Glutamax and 0.1 mM non-essential amino acids and incubate at 37° C. in 5% $CO_2$. Trypsinize and isolate the cells from culture. Resuspend the cells in Hank's balanced salt solution (HBSS), then mix with MATRIGEL® (1:1) Implant the cells ($5\times10^5$/animal) subcutaneously into the rear flank of the mice (female BALB/c mice, Harlan). Measure the tumor volume with a caliper and the body weight twice a week. After tumor volume reaches approximately 200-250 $mm^3$, randomize animals and group into vehicle control and compound treatment groups. Administer the compound (formulated in 1% hydroxyethylcellulose HEC) and 0.25% TWEEN® 80 and 0.05% Antifoam) and vehicle control (1% HEC and 0.25% TWEEN® 80 and 0.05% Antifoam) by oral gavage. Generate dose response by testing compounds at a single time point (2 hours) following a single dose of: 2.7, 8.3, 25, 75, or 150 mg/kg. Perform a time course at the calculated (method detailed below) $TED_{50}$ or $TED_{80}$ dose from a dose response study by sacrificing the mice at multiple time points between 1 hour and 16 hours after a single dose.

Tissue Processing

Harvest tumor tissues and homogenize as described below. Freeze tumor tissues (~100 mg each) in liquid nitrogen and pulverize with a pestle. Place pulverized tissue into a tube (Lysing Matrix A tube, MPBio #6910-100) on dry ice and homogenize in a lysis buffer (0.6 mL each) (150 mM NaCl; 20 mM Tris, pH 7.5; 1 mM ethylenediaminetetraacetic acid (EDTA); 1 mM ethylene glycol tetraacetic acid (EGTA); 1% TRITON® X-100; Protease Inhibitor cocktail (Sigma P8340); Phosphatase Inhibitor Cocktail II (Sigma P5726); Phosphatase Inhibitor Cocktail III (Sigma P0044)) for 25 seconds using a Bio101 FASTPREP® FP120 homogenizer (setting 4.5). Pellet cellular debris and beads by centrifugation at 14,000×g for 10 minutes at 4° C. Transfer the lysate to a new microfuge tube and centrifuge again, at 14,000×g for 10 minutes at 4° C. Transfer centrifuged lysate to a deep-well 96-well plate and keep on ice. Determine the protein concentration for each lysate using a BioRad protein assay (BioRad DC Protein Assay kit #500-0116) as follows. Prepare the working reagent by adding kit reagent S (20 μL) to every 1 mL of kit reagent A needed for the assay. Prepare 3-5 dilutions of a protein standard from 0.2 mg/mL to 1.5 mg/mL protein and generate a standard curve. Pipet 5 μL of standards and samples into a clean, dry microtiter plate. Add 25 μL of working reagent to each well. Add 200 μL of reagent B into each well and agitate for 5 seconds. After 15 minutes, read the absorbance of each well at 750 nM. Protein levels for each well are determined by comparing the absorbance of the sample wells to the standard curve derived from the standard wells. Normalize the tumor lysates to 10 mg/mL with lysis buffer in preparation for analysis of pSMAD2 and total SMAD2/3 by ELISA as method described below.

SMAD ELISA

Tumor lysates are assayed using independent ELISA plates, where one plate is used to determine the total SMAD 2/3 levels and the other plate is used to determine the phospho SMAD 2 levels. While the coating antibody is the same for both plates, the secondary antibody is specific for total SMAD 2/3 or phospho SMAD 2. These plates are referred to collectively as "ELISA plates" and separately as "Total ELISA plate" or "phospho ELISA plate", respectively. Prepare the coating antibody at 2.5 μg/mL in BupH Carbonate-Bicarbonate buffer (anti-SMAD 2/3 monoclonal antibody, BD Biosciences #610843; BupH Carbonate-Bicarbonate from Pierce #28382) and add at 100 μL per well to 96-well immunoplates (Thermo Scientific #439454) and incubate overnight at 4° C. on a platform shaker to generate the ELISA plates. Next, wash the ELISA plates four times with wash buffer (0.5% TWEEN® 20 in tris buffered saline (TBS), pH 8.0 from Sigma #T-9039) and subsequently block with 200 μL per well of blocking buffer (1% bovine serum albumin (BSA) in 1×TBS) at room temperature on a platform shaker for two hours. Wash four times with wash buffer. To the phospho SMAD ELISA plate, add 100 μL per well of tumor lysate or vehicle lysate at 10 mg/ml to the appropriate wells. To the Total ELISA plate, add 98 μL per well of lysis buffer and 2 ul per well of 10 mg/ml tumor lysate or vehicle lysate to the appropriate wells (0.02 mg protein lysate final). A standard curve is also added to each ELISA plate (phospho and total both) using purified pSMAD2. Incubate overnight. Wash the ELISA plates again four times with wash buffer. Prepare secondary antibodies (Millipore anti-phospho SMAD2 rabbit monoclonal antibody #04-953; Millipore anti-SMAD2/3 rabbit polyclonal antibody #07-408) at 1:500 dilution in lysis buffer supplemented with 1% BSA and add 100 μL per well to the appropriate plate. Incubate the plates at room temperature for two to three hours. Wash four times with wash buffer and add 100 μL per well of reporter antibody (anti-rabbit HRP, GE Healthcare #NAV934V, diluted 1:10,000 in blocking buffer) to the plates. Incubate for one hour at room temperature and wash the plates a final four times with wash buffer and add 100 μL per well of room temperature 3, 3',5,5'-tetramethylbenzidine (TMB; Surmodics/BioFX #TMBW-0100-01). Incubate the plates at 37° C. for up to thirty minutes. Stop the reaction with the addition of 100 μL of Stop solution (1N $H_2SO_4$). Read the absorbance (OD) at 450 nm on a plate reader.

Use the ratio of total SMAD (tSMAD) to phospho SMAD (pSMAD) for the vehicle group to determine the minimum inhibition (0%) of pSMAD signal. Calculate the percent inhibition for compound treated groups relative to the minimum pSMAD inhibition of the vehicle group. Calculate $TED_{50}$ and $TED_{80}$ from a dose response study (dose necessary to achieve 50% and 80% inhibition at this time point, respectively) by using NLIN procedure in SAS (Version 9.3, Cary, N.C.). This assay demonstrates that Example 1 has a $TED_{50}$ value of 10.8 mg/kg 2 hours after 1 dose and a $TED_{80}$ of 24.1 mg/kg. In the time course study at the $TED_{50}$ dose (11 pmk), Example 1 demonstrates 48% inhibition at one hour and 39% inhibition at two hours after dosing. In the time course study at (25 mpk), Example 1 demonstrates 71% inhibition at one hour and 70% inhibition at two hours after dosing.

The compounds of the present invention are generally effective over a wide dosage range. For example, dosages per day normally fall within the daily range of about 1-2000 mg. Preferably such doses fall within the daily range of 10-1000 mg. More preferably such doses fall within the daily range of 10-100 mg. Even more preferably such doses fall within the daily range of 10-80 mg. Most preferably such doses fall within the daily range of 10-50 mg. In some instances dosage levels below the lower limit of the aforesaid ranges may be more than adequate, while in other cases still larger doses may be employed, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of the formula:

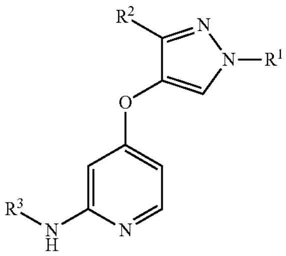

wherein:

$R^1$ is hydrogen, isopropyl, difluoromethyl, difluoroethyl or cyclopropyl;

$R^2$ is tetrahydropyran-4-yl; and $R^3$ is pyridin-2-yl, (1-hydroxy-1-methylethyl)pyridinyl, or 1-methyl-2-oxo-1H-pyridin-4-yl;

or a pharmaceutically acceptable salt thereof.

2. The compound according to claim 1 which is 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol or a pharmaceutically acceptable salt thereof.

3. The compound or salt according to claim 2 which is 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol 4-methylbenzenesulfonate.

4. The compound or salt according to claim 3 which is crystalline 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol 4-methylbenzenesulfonate.

5. The compound or salt according claim 4 which is crystalline 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol 4-methylbenzenesulfonate comprising at least one peak at 17.8° in combination with one or more of the peaks selected from the group consisting of 19.7°, 18.4°, and 22.0° (2θ±0.2°).

6. A pharmaceutical composition comprising a compound of the formula:

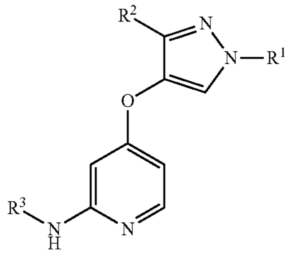

wherein:

$R^1$ is hydrogen, isopropyl, difluoromethyl, difluoroethyl or cyclopropyl;

$R^2$ is tetrahydropyran-4-yl; and $R^3$ is pyridin-2-yl, (1-hydroxy-1-methylethyl)pyridinyl, or 1-methyl-2-oxo-1H-pyridin-4-yl;

or a pharmaceutically acceptable salt thereof;

and one or more pharmaceutically acceptable excipients, carriers, or diluents.

7. A method of treating colon cancer, melanoma, hepatocellular carcinoma, renal cancer, glioblastoma, pancreatic cancer, myelodysplastic syndrome, lung cancer, or gastric cancer in a patient in need of such treatment comprising administering the patient an effective amount 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol or a pharmaceutically acceptable salt thereof.

8. The method according to claim 7 wherein the salt is a 4-methylbenzenesulfonate.

9. A method of treating liver fibrosis or chronic kidney disease in a patient in need of such treatment comprising administering the patient an effective amount of 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol or a pharmaceutically acceptable salt thereof.

10. The method according to claim 9 wherein the salt is a 4 methylbenzenesulfonate.

11. The pharmaceutical composition of claim 6 wherein the compound is 2-{4-[(4-{[1-cyclopropyl-3-(tetrahydro-2H-pyran-4-yl)-1H-pyrazol-4-yl]oxy}pyridin-2-yl)amino]pyridin-2-yl}propan-2-ol or a pharmaceutically acceptable salt thereof.

12. The pharmaceutical composition of claim 7 wherein the salt is a 4-methylbenzenesulfonate.

* * * * *

UNITED STATES PATENT AND TRADEMARK OFFICE

CERTIFICATE OF CORRECTION

PATENT NO. : 9,617,243 B2
APPLICATION NO. : 14/870033
DATED : April 11, 2017
INVENTOR(S) : William T. McMillen et al.

It is certified that error appears in the above-identified patent and that said Letters Patent is hereby corrected as shown below:

At Column 1, Line 1: Please delete “ELi” and insert -- Eli --, therefor.

At Column 2, Line 1: Please delete “Mucosallmmunology” and insert -- MucosalImmunology --, therefor.

At Column 75, Line 61: Please delete “(11 pmk)” and insert -- 11 mpk --, therefor.

At Column 76, Line 58: Please delete “according” and insert -- according to --, therefor.

At Column 78, Line 15: Please delete “4 methylbenzenesulfonate.” and insert -- 4-methylbenzenesulfonate. --, therefor.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*